United States Patent [19]
Jarvik

[11] Patent Number: 6,096,717
[45] Date of Patent: Aug. 1, 2000

[54] METHOD FOR PRODUCING TAGGED GENES TRANSCRIPTS AND PROTEINS

[76] Inventor: Jonathan W. Jarvik, 6419 Beacon St., Pittsburg, Pa. 15217

[21] Appl. No.: 08/745,404

[22] Filed: Nov. 8, 1996

Related U.S. Application Data

[63] Continuation-in-part of application No. 08/000,619, Jan. 5, 1993, Pat. No. 5,652,128.

[51] Int. Cl.[7] .............................. C12N 15/79; C12N 5/10; C12P 19/34; C12P 21/00
[52] U.S. Cl. ........................... 514/44; 435/69.7; 435/325; 435/419; 435/455; 435/468; 435/91.1; 800/8
[58] Field of Search .............................. 514/44; 435/468, 435/455, 69.7, 91.1, 325, 419; 800/8

[56] References Cited

PUBLICATIONS

Theiler, K., The House Mouse: Atlas of Embryonic Development, Springer–Verlag: New York, pp. 148–149, 1989.

Debuchy et al., "The argininosuccinate lyase gene of *Chlamydomonas reinhardtii*: an important tool for nuclear transformation and for correlating the genetic and molecular maps of the ARG7 locus," *The EMBO J.*, 8: 2803–2809 (1989).

Diener et al., "Rescue of a paralyzed flagella mutant of Chlamydomonas by transformation," *Proc. Nat. Acad. Sci. USA*, 87: 5739–5743 (1989).

Karem et al., *Proc. Nat. Acad. Sci.*, USA 87, 8447–8451 (1990).

Kindle, High frequency nuclear transformation of *Chlamydomonas reinhardtii*, *Proc. Nat. Acad. Sci. USA* 87: 1228–1232 (1990).

Kornfeld et al., Structure and expression of a family of Ultrabithorax mRNAs generated by alternative splicing and polyadenylation in Drosophila, *Genes Dev* 3: 243–258 (1989).

Kransnow et al., "Transcriptional activation and repression by Ultrabithorax proteins in cultured Drosophila Cells," *Cell* 57: 1031–1043 (1989).

Nilsson et al., *Journal of Cell Biology* 120: 5–13 (Jan. 1993).

O'Conner et al., "Alternative products from the Ultrabithorax domain of the bithorax complex," *EMBO J.*, 7: 435–455 (1988).

Sanger et al., "DNA sequencing with chain–terminating inhibitors," *Proc. Nat. Acad. Sci. USA*, 74: 5463–5467 (1977).

Silflow et al., "*Chlamydomonas reinhardtii* tubulin gene structure," *Ann. N.Y. Acad. Sci.*, 466: 18–30 (1986).

Soldati et al., *Cell* 66: 277–289 (1991).

Taillon et al., "Mutational analysis of centrin: an EF–hand protein associated with three distinct contractile fibers in the basal body apparatus of Chlamydomonas," *J. Cell Biol.*, 119: 1613–1623 (1992).

Weber et al., *Cell* 36: 983–992 (1984).

(List continued on next page.)

*Primary Examiner*—Scott D. Priebe
*Attorney, Agent, or Firm*—Webb Ziesenheim Logsdon Orkin & Hanson, P.C.

[57] ABSTRACT

The invention described here is a method whereby a molecular tag is put on a gene, transcript and protein in a single recombinational event. The protein tag takes the form of a unique peptide that can be recognized by an antibody or other specific reagent, the transcript tag takes the form of the sequence of nucleotides encoding the peptide that can be recognized by a specific polynucleotide probe, and the gene tag takes the form of a larger sequence of nucleotides that includes the peptide-encoding sequence and other associated nucleotide sequences. The central feature of the invention in its essential form is that the tag-creating DNA has a structure such that when it is inserted into an intron within a gene it creates two hybrid introns separated by a new exon encoding the protein tag. A major virtue of the method is that it allows one to identify new proteins or protein-containing structures, and, having done so, to readily identify and analyze the genes encoding those proteins.

100 Claims, 7 Drawing Sheets

OTHER PUBLICATIONS

Williams et al., "Molecular cloning and sequence analysis of the Chalamydomonas gene coding for radial spoke protein 3: flagellar mutation pf–14 is an ochre allele," *J. Cell Biol.*, 109: 235–245 (1989).

Wilson et al., "The structure of an antigenic determinant in a protein," *Cell* 37: 767–778 (1984).

Wright et al., "A nucleus/basal body connector in *Chlamydomonas reinhardtii* that may function in basal body localization or segration," *J. Cell Biol.*, 101: 1903–1912 (1985).

Adams et al., "Complimentary DNA sequencing: expressed sequence tags and Human Genome Project," *Science*, 252: 1651–1656 (1991).

Adams et al., "Sequence identification of 2.375 human brain genes," *Nature* 355: 632–634 (1992).

Botstein et al., "Construction of a genetic linkage map in man using restriction fragment length polymorphisms," *Am. J. Hum. Genet.* 32: 314–331 (1980).

Charbit et al., Probing the topology of a bacterial membrane protein by genetic insertion of a foreign epitope: expression at the cell surface. *EMBO J.*, 5: 3029–3037 (1986).

Chen et al., "High–efficiency transformation of mammalian cells by plasmid DNA," *Mol. Cell. Biol.* 7: 2745–2752 (1987).

Colbere–Garapin et al., "Patterns of integration of exogenous DNA sequences transfected into mammalian cells of primate and rodent origin," *Gene*, 50: 279–288 (1986).

Cooley et al., "Insertional mutagenesis of the Drosophila genome with single P elements," *Science*, 239: 1121–1128 (1988).

Craik et al., "Splice junctions: association with variations in protein structure," *Science*, 220: 1125–1129 (1983).

Duyk et al., Exon trapping: a genetic screen to identify candidate transcribed sequences in cloned mammalian genomic DNA, *Proc. Nat. Acad. Sci. USA*, 87: 8995–8999 (1990).

Field et al., "Purification of a RAS–responsive adenylyl cyclase complex from *Saccharomyces cerevisiae* by use of an epitope addition method," *Mol. Cell Biol.*, 8: 2159–2165.

Freimuth et al., "Codon insertion mutants of the adenovirus terminal protein," *Proc. Nat. Acad. Sci.* 7816–7820 (1986).

Freimuth et al., "Introduction of guest peptides into *Escherichia coli* alkaline phostase," *J. Biol. Chem.*, 265: 896–901 (1990).

Friedrich et al., "Promoter traps in embryonic stem cells: a genetic screen to identify and mutate developmental genes in mice," *Genes and Dev.*, 5: 1513–1523 (1991).

Gossler et al., "Mouse embryonic stem cells and reporter constructs to detect developmentally regulated genes," *Science*, 244: 463–465 (1989).

Green et al., "Biochemical mechanisms of constitutive and regulated pre–mRNA splicing," *Ann. Rev. Cell Biol.*, 7: 559–599 (1991).

Grimwade et al., "Gene expression and protein localization in yeast," 16th Int. Conf. on yeast genetics and molecular biology: S695, (1992).

Hawkins, "A survey on intron and exon lengths," *Nucleic Acids Res.*, 16: 9893–9910 (1988).

Hochgeschwender et al., "Identifying genes within the genome: new ways for finding the needle in the haystack," *BioEssays*, 13: 139–144 (1991).

Lobel, "Construction of mutants of Malony murine leukemia virus by suppressor–linked Insertonal mutagenesis: positions of viable insertion mutations," *Genetics* 81: 4149–4153 (1984).

Luehrsen et al., "Insertion of non–intron sequence into maize introns interferes with Splicing," *Nucl. Acids Res.*, 20: 5181–5187.

Munro et al., "Use of peptide tagging to detect proteins expressed from cloned genes: deletion mapping functional domains of Drosophilia hsp70," *EMBO J.*, 3: 3087–3093 (1984).

Murnane et al., Recombination events during integration of transfected DNA into normal human cells, *Nucleic Acids Res.*, 18: 2733–2738 (1990).

O'Kane et al., Detection in situ of genomic regulatory elements in Drosophilia, *Proc. Nat. Acad. Sci. USA*, 84: 9123–9127 (1987).

Rommens et al., "Identification of the cystic fibrosis gene: chromosome walking and jumping," *Science* 245: 1059–1065 (1989).

Snyder et al., "λgt11: gene isolation with antibody probes and other applications," *Methods in Enzymology*, 154: 107–128 (1987).

R: purine; Y: pyrimidine; N: any base.

METHOD FOR PRODUCING TAGGED GENES TRANSCRIPTS AND PROTEINS

The present application is a Continuation-in-Part specification based on U.S. application Ser. No. 08/000,619, now issued U.S. Pat. No. 5,652,128.

References cited.
1. Botstein et al. (1980) *Am. J. Hum Genet.*, 12: 314.
2. Karem et al. (1990) *Proc. Nat. Acad. Sci. USA,* 87: 8447.
3. Cooley et al. (1988) *Science* 239: 1121.
4. Weber et al. (1984) *Cell,* 36: 983.
5. Soldati and Perriard (1991) *Cell,* 66: 277.
6. Snyder et al. (1987) *Methods in Enzymology,* 154: 107.
7. Adams et al. (1991) *Science,* 252: 1651.
8. Green (1991) *Ann. Rev. Cell Biol.,* 7: 559.
9. Gossler et al. (1989) *Science,* 244: 463.

1. Field of the Invention

This invention relates to the fields of Molecular Biology and Molecular Genetics with specific reference to the identification and isolation of proteins and of the genes and transcripts that encode them.

2. Description of the Prior Art

The primary area of the invention—the identification and tagging of genes and proteins—has received a great deal of attention, and many successful methods have been devised. None of these methods, however, has the feature of tagging gene, transcript and protein in a single event.

Linkage Analysis

Genes have traditionally been identified by identifying mutations and then mapping them with respect to one another by means of genetic crosses. This kind of mapping, or linkage analysis, does not serve to isolate the genes themselves nor does it indicate anything about the genes' molecular structure or function. In recent years a form of linkage analysis using restriction fragment length polymorphisms (RFLPs) has come into use (1). This method serves to identify DNA sequences that are linked to a gene of interest, and, having identified such a DNA sequence, it is possible in principle, and sometimes in practice, to identify and clone the gene itself by performing chromosome walks or jumps (2). It should be stressed that, even when successful, this strategy identifies the gene, not the protein encoded by the gene.

Transposon Tagging

Another technique for cloning genes that has been developed relatively recently goes by the name transposon tagging. In this technique (3), mutations due to the insertion of transposable elements into new sites in the genome are identified, and the genes in which the transposons lie can then be cloned using transposon DNA as a molecular probe. Transposon tagging, like RFLP/linkage analysis, identifies genes, not proteins.

Enhancer Trapping

Another method for identifying genes, enhancer trapping (4), involves the random insertion into a eucaryotic genome of a promoter-less foreign gene (the reporter) whose expression can be detected at the cellular level. Expression of the reporter gene indicates that it has been fused to an active transcription unit or that it has been inserted into the genome in proximity to cis-acting elements that promote transcription. This approach has been important in identifying genes that are expressed in a cell type-specific or developmental stage-specific manner. Enhancer trapping, like RFLP/linkage analysis and transposon tagging, identifies genes, not proteins, and it does not directly reveal anything about the nature of the protein product of a gene.

Guest Peptides and Epitope Tagging

A number of studies have been performed in which new peptides have been inserted into proteins at a variety of positions by modifying the genes encoding the proteins using recombinant DNA technology. The term "guest peptide" has been used to describe the foreign peptides in these cases. It is clear that in many cases the presence of such peptides is relatively innocuous and does not substantially compromise protein function—especially in those cases where the peptide is on the surface of the protein rather than in its hydrophobic core.

Epitope tagging (5) is a method that utilizes antibodies against guest peptides to study protein localization at the cellular level and subcellular levels. Epitope tagging begins with a cloned gene and an antibody that recognizes a known peptide (the epitope). Using recombinant DNA technology, a sequence of nucleotides encoding the epitope is inserted into the coding region of the cloned gene, and the hybrid gene is introduced into a cell by a method such as transformation. When the hybrid gene is expressed the result is a chimeric protein containing the epitope as a guest peptide. If the epitope is exposed on the surface of the protein, it is available for recognition by the epitope-specific antibody, allowing the investigator to observe the protein within the cell using immunofluorescence or other immunolocalization techniques. Epitope tagging serves to mark proteins of already-cloned genes but does not serve to identify genes.

Isolating Genes Beginning with the Proteins they Encode

A number of procedures have been developed for isolating genes beginning with the proteins that they encode. Some, such as expression library screening (6), involve the use of specific antibodies that react to the protein of interest. Others involve sequencing all or part of the protein and designing oligonucleotide probes that can be used to identify the gene by DNA/DNA hybridization. In all of these cases, one must have specific knowledge about a protein before it is possible to take steps to clone and characterize the gene that encodes it.

cDNA Cloning and Sequencing

A method of gene identification that has received a great deal of attention in the recent past is the cloning (and in many instances, sequencing) of so-called expressed sequence tags (ESTs) from cDNA libraries made from mRNA extracted from a given tissue or cell type (7). Information about the proteins encoded by the mRNAs can be derived from the cDNA sequences by identifying and analyzing their open reading frames. In many cases such cDNAs are not full length, however, and so information about the amino-terminal portion of the protein is lacking. And, more significantly, the method tags transcript sequences and not the proteins that the transcripts encode.

RNA Splicing

RNA splicing is the natural phenomenon, characteristic of all eucaryotic cells, whereby introns are removed from primary RNA transcripts. A large body of research has revealed that an intron is functionally defined by three components—a 5' donor site, a branch site and a 3' acceptor site (8). If these sites are present, and if the intron is not too large (it can be at least as large as 2 kb in many organisms), and if the distance between the branch and 3' acceptor sites is appropriate, the cellular splicing machinery is activated and the intron is removed from the transcript. Many different natural DNA sequences are known to have splice site function; consensus sites for mammalian splicing are indicated in FIG. 1. Thus, not only have many active splice sites been cloned, but there is a large database that can be used to design synthetic functional splice site sequences.

FIG. 1. Consensus sequences for splicing mammalian pre-mRNA transcripts.

R: purine; Y: pyrimidine; N: any base.

Gene Trapping

Gene trapping is a method used to identify transcribed genes. Gene trapping vectors carry splice acceptor sites directly upstream of the coding sequence for a reporter protein such as b-galactosidase. When the vector inserts into an intron of an actively transcribed gene, the result is a protein fusion between an N-terminal fragment of the target gene-product and the reporter protein, the activity of which is used as an indicator that integration into an active gene has occurred (9). Gene trapping seeks to identify transcribed genes—not to tag proteins, and to inactivate genes—not to produce an active tagged gene product.

OBJECTS AND ADVANTAGES OF THE INVENTION

"CD-DNA" and "CD-Tagging"

The so-called central dogma of genetics states that information flows from DNA to RNA to protein. The method of this invention tags each of the classes of macromolecule included in the central dogma. Accordingly, the method is referred to herein as "CD-tagging." Likewise, the term "CD-DNA" is used herein to refer to a DNA molecule that is inserted into the genome using the method of this invention.

Identifying and Isolating Proteins, RNAs and Genes

A method that allows one to readily identify genes by observing tagged proteins ought to be of great advantage relative to the prior art. CD-tagging has just this feature. In particular, when the protein tag is an epitope that is recognized by a particular antibody, cells can be treated with a CD-DNA, or with DNA constructs containing a CD-DNA, and then subjected to immunological screens or selections to identify the epitope tag. Many different screens or selections are possible, each of which has its own particular advantages. These include direct or indirect immunofluorescence by which tagged proteins can be localized to particular regions or subcellular structures within a cell, immunoblot analysis by which the abundance, molecular weight and isoelectric points of tagged proteins can be determined, enzyme linked immunoassays (ELISAs) by which internal or secreted tagged proteins can be distinguished, and fluorescence-activated cell sorting (FACS) by which living cells with tagged proteins at their surfaces can be obtained.

Once proteins and genes of interest have been identified, they can be efficiently purified using standard hybridization and/or affinity-purification methods that take advantage of their specific tags.

Large Target Size in the Genome

CD-tagging depends on the insertion of a CD-DNA into an intron. Since higher eucaryotic genes contain much more intron than exon sequence, the target size is large relative to any other tagging method in which the DNA must insert into an exon. Further, since the typical gene contains numerous introns, the boundaries of which determine the sites at which amino acid insertions in the protein can be produced by CD-tagging, it is likely that for a given protein there exist multiple sites at which peptide tags produced by CD-DNA insertions would not seriously compromise protein function. Indeed, there is some evidence that the sites in many proteins that are determined by the exon/intron boundaries are particularly likely to be on the surface of the protein—at an ideal location to accept a guest peptide and to allow recognition of that peptide by an antibody.

Hybrid Proteins are Expressed in Backgrounds where Normal Genes Are Also Present As discussed earlier, experience has shown that in many, and perhaps most, cases epitope fusion proteins have normal, or nearly normal, activity. But even this is not a requirement in order for CD-tagging to be useful in identifying proteins and their genes because in many applications one or more copies of the normal gene will be present in addition to the tag-containing gene (e.g., when diploid cells are tagged); here the tagged protein need not be fully functional as long as it can, for example, co-assemble at its normal location along with the protein encoded by the unaltered gene.

Obtaining Sequence Data

Once an organism or cell line expressing a protein of interest has been identified using the method of the invention, a DNA representing a portion of mRNA encoding the protein can be obtained by standard techniques such as plasmid rescue or amplifying the sequence of interest from cDNA by means of the polymerase chain reaction (PCR) using poly-dT as one primer and a DNA complimentary to the tag-encoding sequence as the other. The amplified DNA can then be sequenced by standard methods. Knowledge of the sequence can then be used to design primers for amplification from genomic DNA in order to obtain genomic sequence information.

Application to Analysis of Subcellular Structures

One important application for CD-tagging is to identify proteins, and the genes encoding them, that are present in particular subcellular structures. This can be done by screening CD-DNA recipients for those that express the protein tag in the structure of interest. A significant advantage of this approach is that it does not depend upon the purification of the structure of interest, or even on the prior existence of a method for such purification, as traditional methods for characterizing subcellular structures do.

In addition to identifying proteins in known structures, CD-tagging holds the promise of identifying new structures, and the proteins they contain, that have not been explicitly recognized before.

Application to the Analysis of Cellular Responses

CD-tagging can be used to identify proteins, and the genes encoding them, whose synthesis is stimulated by a particular treatment, such as the administration of a particular hormone or growth factor to a particular cell type. This can be accomplished by comparing treated and untreated cells to identify proteins whose levels change in response to the treatment. And, using standard immunocytochemical methods, one can discriminate among such proteins to identify those that are secreted, localized to the cell surface, or present in particular subcellular compartments.

Application to Virology

Viral infection often leads to specific changes in cellular gene expression. Using CD-tagging, cellular genes whose expression is up or down-regulated can be identified by comparing the levels of tagged proteins in infected versus uninfected cells. Likewise, if the viral genome is tagged, the expression of viral proteins during the viral life cycle can be observed.

Application to Analysis of Transcriptional Regulation

Much genetic regulation occurs at the level of transcription. Because CD-tagging puts a unique tag into mRNA species derived from a tagged gene, the tag can be used to investigate mRNA synthesis and stability.

Application to the Analysis of the Human Genome

Because most cellular functions are mediated by proteins, it is of particular interest in the context of the comprehensive analysis of the human genome to identify those parts of the genome that are expressed in the form of proteins. CD-tagging provides an efficient general method to directly identify new genes on the basis of their expression as proteins and on the basis of the location of those proteins in particular cellular or extracellular structures. In addition, CD-tagging provides a method for efficient physical and/or RFLP mapping of genes, as well as a method for the isolation of genes and transcripts via their nucleic acid tags and for the efficient purification of proteins via their epitope tags. CD-tagging has specific advantages over the prior art method for identifying and mapping genes using expressed sequence tags (ESTs). ESTs are cDNA sequences, not genomic sequences. Thus an EST probe will hybridize not only to the true gene but to any pseudogenes that are present in the genome, thereby limiting its usefulness for mapping and cloning the true gene. Likewise, an EST probe may hybridize with closely related members of a gene family, again limiting its usefulness as a probe for a unique sequence. These limitations do not apply if a gene is identified by CD-tagging, since the method provides direct access, through the CD-DNA tag, to the true gene.

Applications to Medicine

CD-tagging has broad application to the analysis and diagnosis of disease. With regard to analysis, CD-tagging makes it possible to demonstrate, through linkage analysis, that a defect with respect to a given protein represents the primary defect for a given genetic disease or cancer. The function of the protein can then be examined in detail to gain new understanding of the biology of the disease.

With regard to diagnosis, genes that are isolated using CD-tagging can provide probes to identify disease-associated restriction fragment length polymorphisms, and they can provide primers by which mutations responsible for genetic diseases could be precisely identified. Once such polymorphisms or mutations have been identified, diagnostic tests for the presence of mutant alleles in homozygous or heterozygous individuals can be developed using standard approaches. Likewise, proteins that are isolated using the invention can be used as antigens to develop antibodies that can be used to make molecular diagnoses for a particular genetic disease. With regard to therapy, genes or proteins that are identified using CD-tagging could be used to treat a wide variety of infectious and non-infectious diseases.

SUMMARY OF THE INVENTION

The invention utilizes a "CD-DNA" molecule that contains acceptor and donor sites for RNA splicing. Between the acceptor and donor sites is a sequence of nucleotides that encodes a particular peptide (or set of three peptides, one for each possible reading frame). When the CD-DNA is inserted into an existing intron, it creates a new peptide-encoding exon surrounded by two hybrid, but functional, introns. The result is that, after transcription, RNA splicing and translation, a protein is produced that contains the peptide located precisely between the amino acids encoded by the exons that surrounded the target intron. Thus, in a single recombination event at the DNA level: 1) the gene encoding the protein is tagged by the CD-DNA sequence for recognition by a DNA probe or primer, 2) the RNA transcript encoding the protein is tagged by the peptide-encoding sequence for recognition by a DNA probe or primer, and 3) the protein is tagged by the peptide for recognition by a specific antibody or other reagent.

In the Figures the various DNA segments ("peptide-encoding segment," "left arm," "right arm," "central segment") are not given specific lengths. This reflects the fact that their lengths can vary considerably and need not have the same values from embodiment to embodiment. The peptide encoding segments will generally be between 24 and 75 nucleotides in length so as to encode peptides of 8 to 25 amino acids; the other segments will generally be between 100 and 1000 base pairs in length so that the hybrid introns created by insertion of the CD-DNA are not too large for efficient splicing. Likewise the base compositions of the various DNA segments are not defined, except at the indicated splice acceptor, branch and donor sites. These segments could be random sequences or be natural sequences without unusual structural features.

It should be emphasized that a great many different molecules of the structures claimed here can be constructed, and that a great many specific means for constructing such molecules using standard recombinant DNA technology will be obvious to an individual skilled in the arts of molecular biology.

DETAILED DESCRIPTION OF INVENTION

This invention provides a method for tagging proteins and the genes and transcripts that encode them in a single recombinational event. The method involves the insertion by in vitro or in vivo recombination of a specially chosen and/or designed DNA sequence into an intron that is expressed within the genome of a cell or organism. This DNA sequence carries: 1) coding information for one or more specific peptides, typically, but not necessarily, from eight to twenty-five amino acids in length, and 2) appropriately placed branch, acceptor and donor sites for RNA splicing. The nucleotide sequences representing the branch, acceptor and donor sites may represent natural sites taken from known genes or they may be rationally designed based on current knowledge of the nucleotide compositions of such sites (8).

FIGS. 2–8 show the structures of a number of different embodiments of the invention. A key and essential feature of these embodiments is that, when inserted into existing introns, they instruct the splicing machinery of the cell to recognize more than one intron where there was previously one, with these new introns flanking a new exon, or exons, encoding a peptide, or peptides, of determined amino acid sequence.

All of these embodiments can be readily produced by an individual skilled in the arts of molecular biology. I have not specified the specific means by which the embodiments are constructed because there are numerous ways, well known to an individual skilled in the arts of molecular biology, by which this can be accomplished. Likewise, I have not specified the particular nucleotide sequences present in each segment, except as specifically indicated in the text. Again, there are many sequences that could serve and that could be used by one skilled in the arts of molecular biology.

Figure 1:
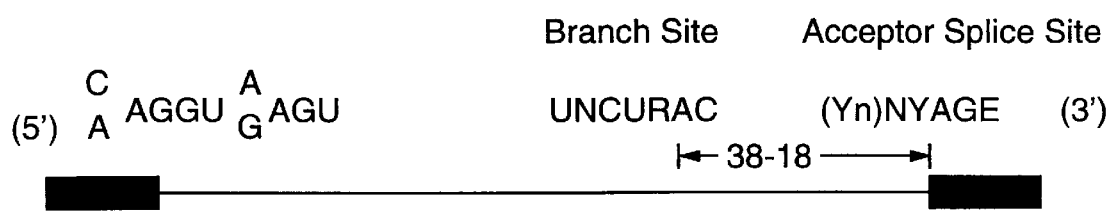
FIG. 1 is a schematic diagram of a gene having a donor splice site, a branch site and an acceptor splice site.
Figure 2:
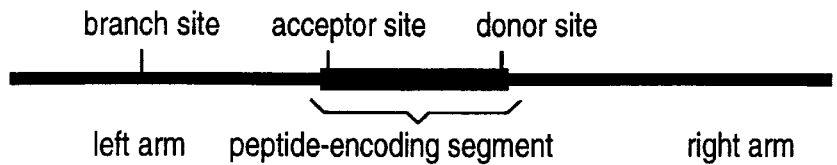
FIGS. 2–8 show the structures of a number of DNA molecules that embody the invention. The dark lines represent DNA molecules, with the thicker areas representing coding sequence. Sites in the DNA are represented by short vertical lines. Segments of each DNA are indicated below each molecule. When the DNAs are functioning when inserted into introns, transcription is from left to right for those regions where the sites are shown above the DNA molecules, and from right to left for those regions where the sites are shown below the DNA molecules.

FIG. 2 represents a simple embodiment of the invention. The DNA is designed to function when inserted into an intron that is transcribed from left to right. It has a peptide-encoding segment between splice acceptor donor sites. Within the left arm is a splice branch site. The size and nucleotide sequence of the peptide-encoding region determines the size and amino acid sequence of the encoded peptide, with the amino acid sequence of the peptide determined by the rules of the genetic code. The number of nucleotide pairs in the peptide-encoding region must be an even multiple of three to ensure that the reading frame is maintained with respect to the surrounding exons.

Figure 3:
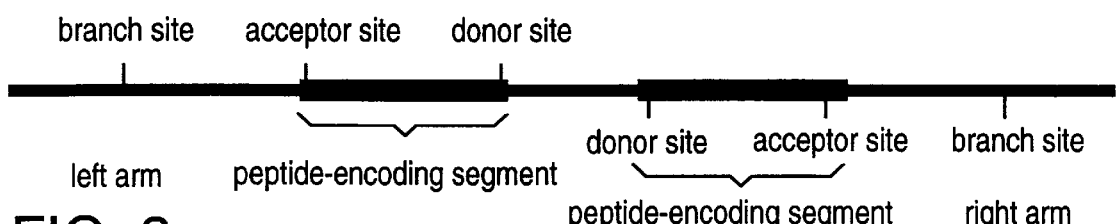
Figure 4:
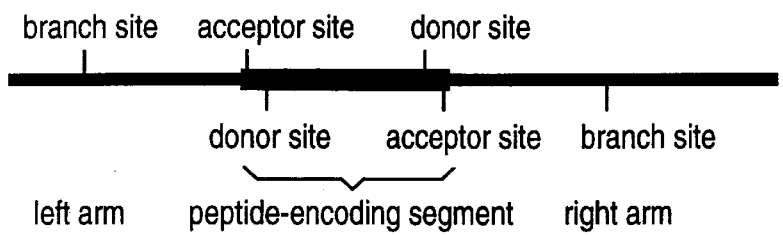
Figure 5:
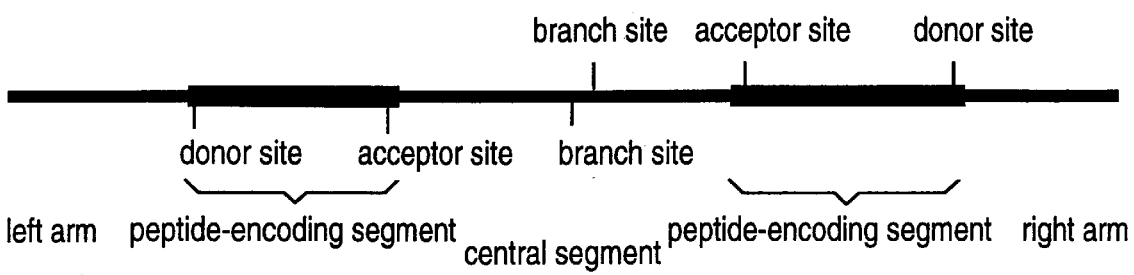

FIGS. 3, 4 and 5 represent embodiments designed to function when inserted into an intron in either orientation.

Figure 6:
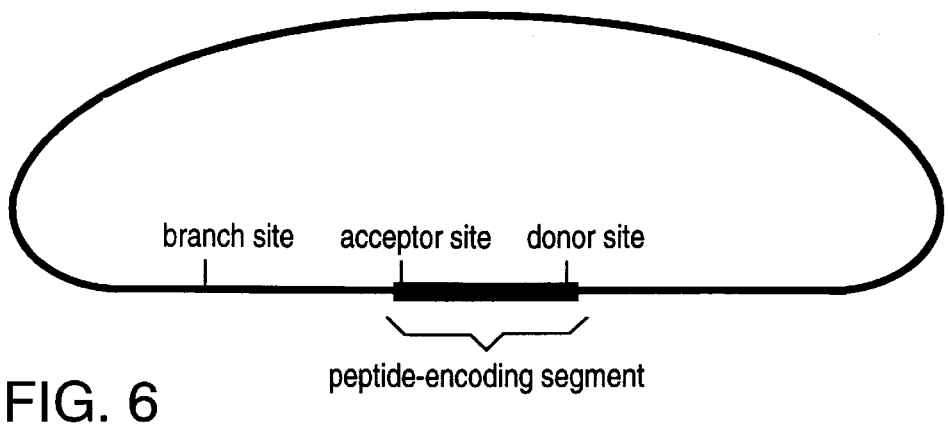

FIG. 6 represents a circular embodiment of the invention. This embodiment could, for example, be a plasmid that contains DNA encoding the guest peptide.

Figure 7:
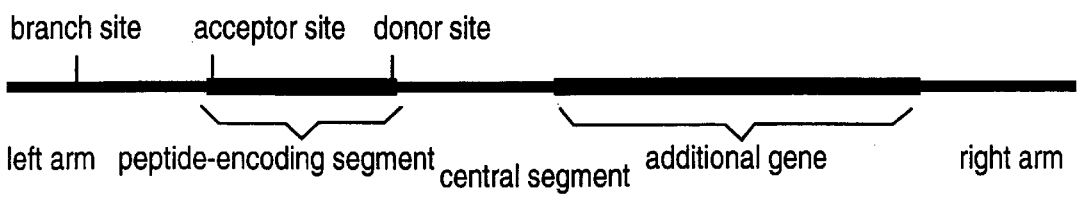

FIG. 7 represents an embodiment incorporating a gene, or genes, that could allow for selection in a target cell. The gene is intron-less so that it does not contribute splice sites.

Figure 8:
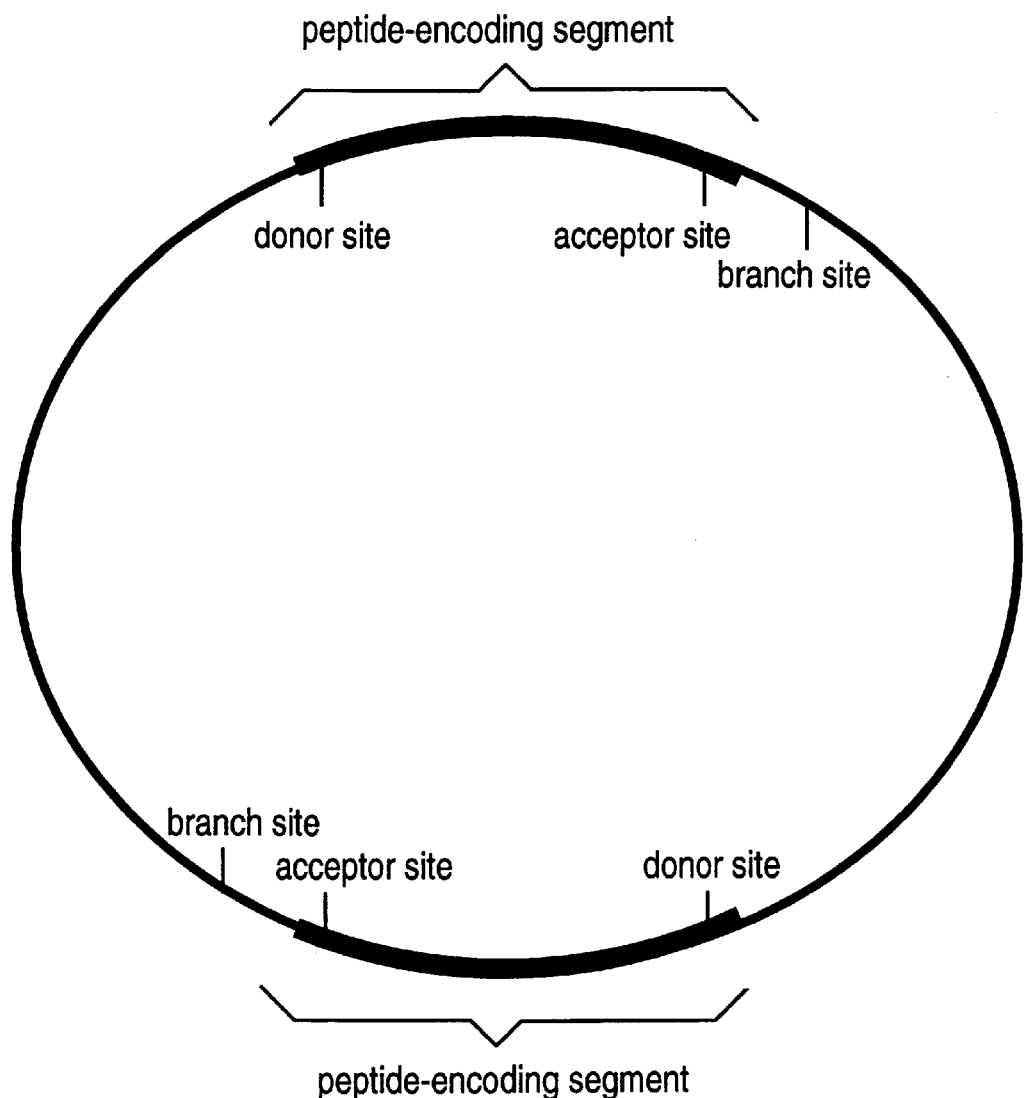

FIG. 8 represents a circular embodiment of the invention containing two peptide-encoding segments.

Figure 9:
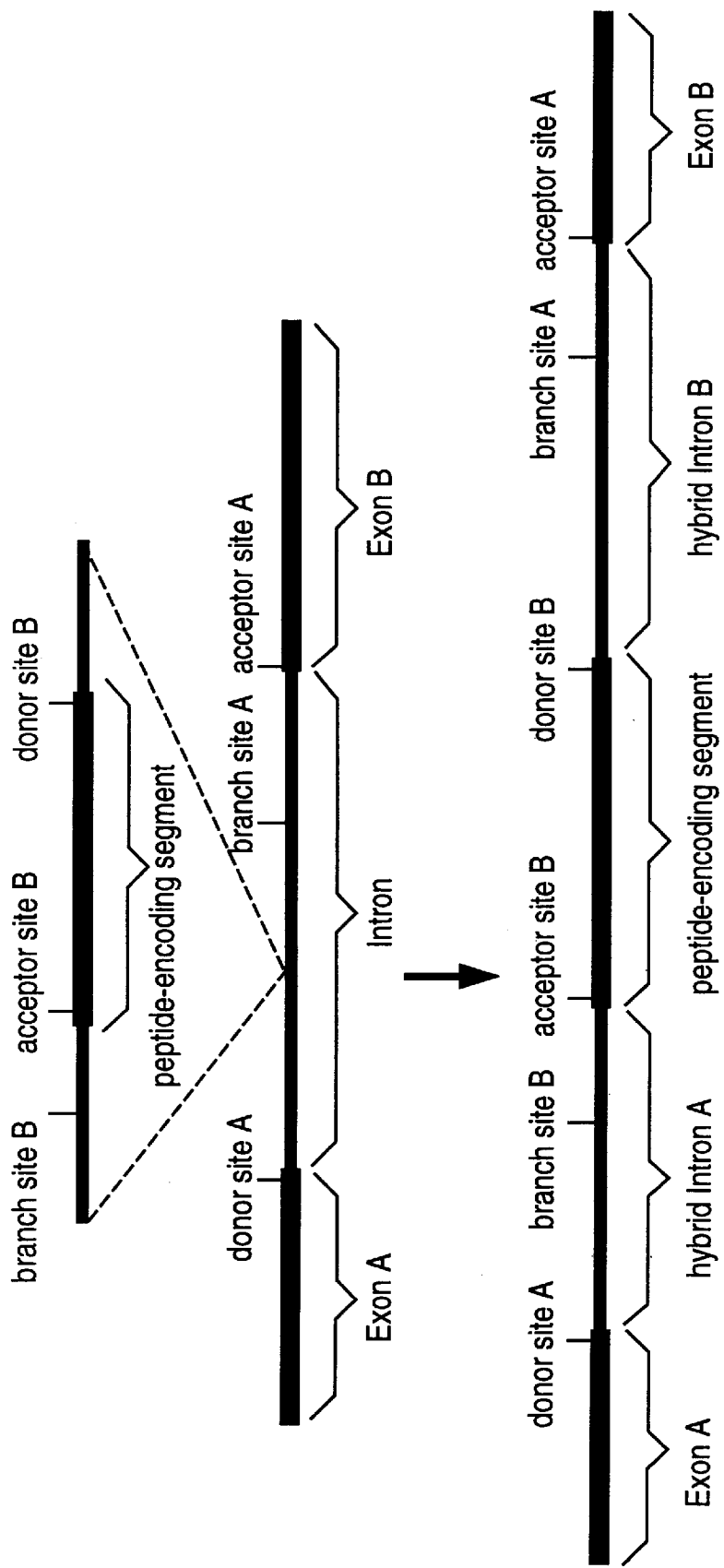
FIG. 9 is a schematic diagram of a CD-DNA inserted into an intron.

FIG. 9 is a schematic diagram of a CD-DNA inserted into an intron.

Figure 10:
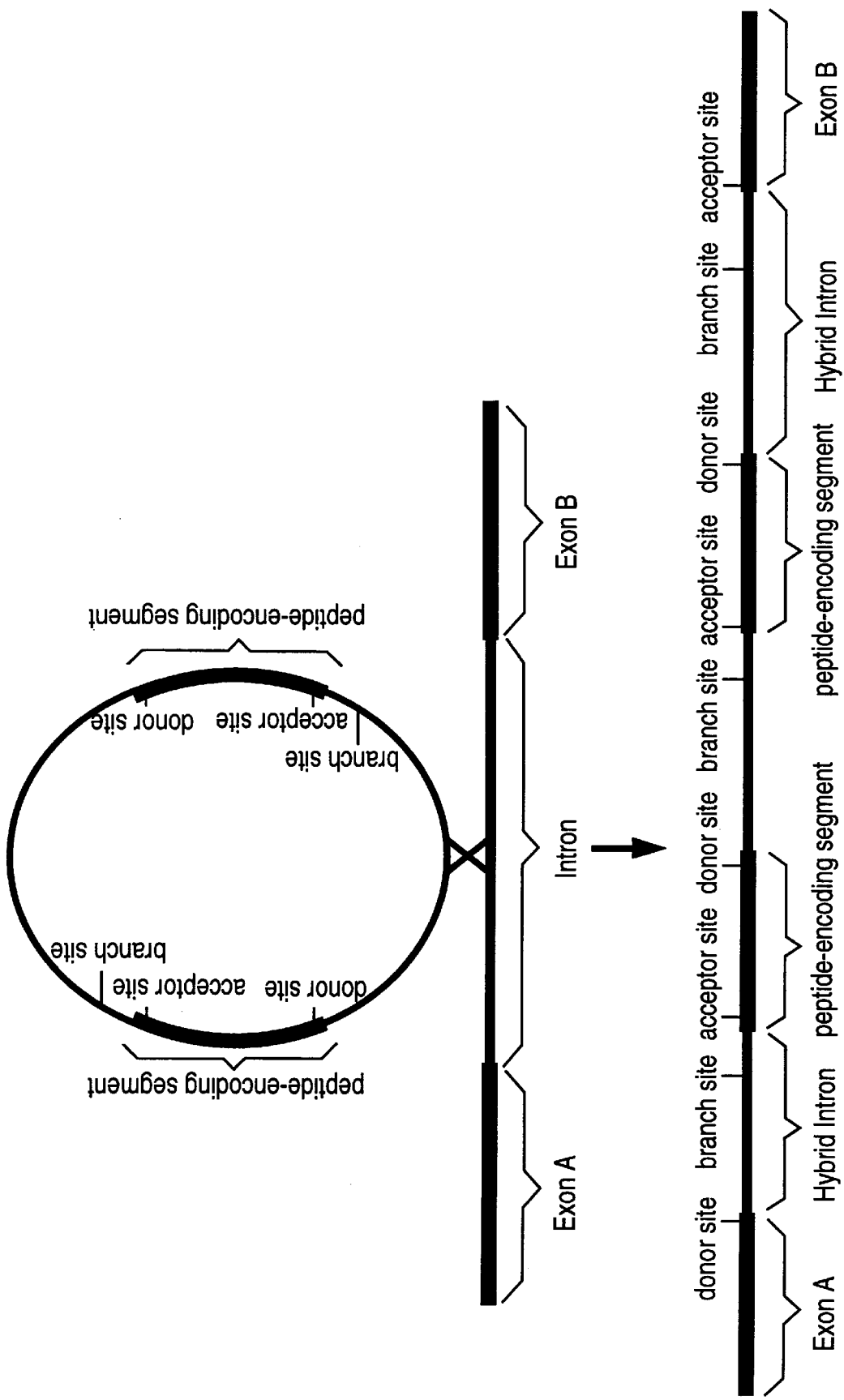
FIG. 10 is a schematic diagram showing the circular embodiment of FIG. 8 inserted into an intron.

FIG. 10 is a schematic diagram showing the circular embodiment of FIG. 8 inserted into an intron.

FIGS. 2 through 8 represent some, but by no means all, possible embodiments of the invention.

More complex embodiments that retain the essential elements of the invention are also possible. For example, CD-DNAs containing more than two segments encoding guest peptides can be designed; such CD-DNAs could be relatively large and yet not lead to the generation, in the target gene, of new introns that are excessively large for efficient splicing.

Likewise, it may be, for example, that in certain cells the branch sites are less critical to splicing function than the acceptor and donor sites, in which case an effective embodiment of the invention might be created without specific branch sites. Thus, as knowledge of the biochemistry of RNA splicing accumulates in the art, DNA sequence features may be identified that can increase the efficiency of CD-tagging. The scope of this invention is intended to include such features.

Operation of the Invention

The design of the CD-DNA is such that when it is inserted into an existing intron, it creates, within the intron, a new peptide-encoding exon. The result is that, after transcription, RDA splicing and translation, a protein is produced that contains the peptide located precisely between the amino acids encoded by the exons that surrounded the target intron. Thus, in a single recombination event: 1) the gene encoding the protein is tagged by the CD-DNA sequence for recognition by a DNA probe or primer, 2) the RNA transcript encoding the protein is tagged by the peptide-encoding sequence for recognition by a DNA probe or primer, and 3) the protein is tagged by the peptide for recognition by a specific antibody or other reagent.

Delivery, Recombination and Function of CD-DNAs

Recombination of a CD-DNA within an intron is essential to successful CD-tagging. FIG. 9 illustrates the structure of the DNA that results from the integration of a linear CD-DNA within an intron by recombination at its ends. When transcribed, this DNA yields an RNA that is spliced to produce an mRNA encoding a protein that contains a guest peptide located precisely between the protein segments encoded by the exons that bound the target intron. FIG. 10 illustrates the structure of the DNA that results from the integration of a circular CD-DNA within an intron by a single crossover. When transcribed, this integrated DNA yields an RNA that is spliced to produce an mRNA encoding a protein that also contains a guest peptide (in this case encoded in two guest exons) located precisely between the protein segments encoded by the exons that bound the target intron.

Integration of a CD-DNA can be accomplished in a number of ways. One approach involves the introduction of CD-DNA into cells by standard methods such as transformation, electroporation, transfection, bulk loading, or liposome fusion, followed by nonhomologous recombination of the CD-DNA into the genome. The occurrence of such recombination is well known in many cell types; sometimes the integration of foreign DNA is accompanied by a small deletion of the target sequence, but, as long as such a deletion remains within the intron, it will present no problem. In another approach, the CD-DNA is inserted by standard in vitro recombination methods into a genomic library in a viral or plasmid vector, and the recombinant plasmids or viruses are then introduced into cells where the recombinant genes are expressed. Yet another approach takes advantage of the mobility of transposons; in this case the CD-DNA is located on a transposon that moves it to new sites in the genome via transposon insertion.

Peotides and Epitopes

In one major class of application of CD-tagging, the peptide that is introduced into a protein is an epitope that is recognized by a specific monoclonal or polyclonal antibody.

In principle, almost any amino acid sequence not present in the cells of interest could serve as such an epitope. And, while there may not be a single "optimal" epitope, epitope design could still follow a rational basis. In most cases, it would be valuable for the epitope to be on the surface of the protein where: 1) it would be readily available to the antibody combining site, and 2) it would minimally disrupt the tertiary structure of the protein as a whole. Surface location can be promoted by use of hydrophilic epitopes (except in the case of integral membrane proteins, where hydrophobic epitopes can be employed). If a single repeating nucleotide is used to encode the epitope, it will yield the same poly-amino acid epitope in all three reading frames; a repeating dinucleotide will encode two potential poly-amino acid epitopes, and a repeating trinucleotide, three such epitopes. A somewhat more complex repeating sequence can be used to encode repeating di-amino acid epitopes, and still more informationally complex sequences can be used to create epitopes of a very wide variety of amino acid sequences, with the only obvious requirement being the absence of stop codons in the reading frames. Furthermore, some CD-DNAs (FIGS. 3, 4, 5) contain peptide-encoding sequences that can be read in both directions; in these cases as many as six distinct epitopes can be encoded on the same CD-DNA. Which epitope appears in the protein will then depend on the orientation the CD-DNA as well as the reading frame that is dictated by the specifics of the intron/exon boundaries of the target intron.

In addition to using epitopes that are designed according to the principles outlined above, other epitopes exist, such as hemagglutinin sequences from influenza virus, micro-exon 1 encoded sequence from the ubx gene of Drosophila, or sequences encoded by the myc oncogene, that have already proved their worth in epitope tagging. These very sequences can be used in embodiments of CD-tagging, thereby ensuring that the guest peptides can be identified by standard procedures.

Recipient Cells

Because RNA splicing is a universal characteristic of eucaryotic cells, CD-tagging is applicable to a very wide variety of cells and organisms, including yeasts, protozoans, algae, metazoans (both plant and animal), and somatic and germline cells derived from metazoan organisms. Because the nucleotide sequences that are necessary and sufficient for splicing are highly conserved across the eucaryotes, it is likely that in many cases the same CD-DNA will function in a variety of cell types and organisms. This is not to say, however, that a given CD-DNA will not function optimally in a given cell type or organism, and so it may prove useful to develop different CD-DNAs for use in different backgrounds. It is also the case that the signals for alternative splicing may vary from cell to cell; the optimal CD-DNA would typically be one in which splicing of the hybrid transcript always occurs. One way to maximize the likelihood of this is to construct the CD-DNA using nucleotide sequences that are known to function in the very background in which the tagging is to be performed.

Identification of Genes and Proteins

Generation of Frameshift Mutations in CD-tagged Genes

1. Jarvik et al. (1996) *Biotechniques* 20: 896.
2. Wang et al. (1996) *Proc. Nat. Acad. Sci. USA* 93: 3932.
3. Lasko et al. (1992) *Proc. Nat. Acad. Sci. USA*, 89: 6232.
4. Lasko et al. (1992) *Proc. Nat. Acad. Sci. USA*. 93: 5860.
5. Gu et al. (1994) *Science,* 265: 103.
6. Rajewsky et al. (1996) *J. Clin. Invest.,* 98: 600.
7. Fridell and Searles (1991).
8. Chou and Perrimon (1992).
9. Golic and Lindquist (1989).
10. Robertson et al. (1988).

Field of the Invention

This invention relates to the fields of Molecular Biology and Molecular Genetics with specific reference to generating frameshift mutations in CD-tagged genes.

Introduction

A fundamental concern in genetics and molecular biology is establishing the correspondence between gene and protein. Thus when a new gene is discovered it is usually desirable to identify the protein or proteins it encodes; conversely, when a new protein is discovered it is usually desirable to identify the gene that encodes it. CD-tagging is a molecular-genetic method that adds specific tags to gene, mRNA and protein in a single recombinational event. The CD-cassette or cassettes can be delivered directly to cells by transfection or transformation, or they may be incorporated into delivery vectors such as viruses or transposons. Using the CD-tagging method, establishing the correspondence between gene and protein in gene discovery is dramatically simplified due to the fact that gene and gene product are discovered together.

Another fundamental concern in genetics and molecular biology is establishing the function of genes and gene products. The CD-tagging method gives important functional information—namely the location of gene products at the tissue, cell and subcellular levels—but it does not, in and of itself, indicate the consequences to the cell and organism of reducing or abolishing gene function. Such information—which is critical to assigning or confirming gene function—must be gained through the analysis of mutant phenotypes or through the analysis of mutant phenocopies.

CD-tagging targets introns using one or more CD-cassettes that contain intronic splice branch, acceptor and donor sites surrounding an internal exon (Jarvik et al. 1996). In this application I describe the structure and use of genetic elements that, when incorporated in the appropriate intronic portions of tandem the CD-cassettes, allow one to create OR REMOVE frameshift mutations and thereby gain critical information about gene function.

Use of Site Specific Recombination to Alter Expression and Function of CD-Tagged Genes Analysis of gene function via mutant analysis is an approach of undisputed utility. Accordingly, it would be of great value to be able to experimentally eliminate the function of a CD-tagged gene after it has been tagged and analyzed. One way that this can be accomplished is to tag with a pair of cassettes that include, in one of them, target sites for site-specific recombination within the intronic portions of the molecule.

Several site-specific recombination systems are known and have been shown to function in a wide variety of procaryotic and eucaryotic organisms and cell types including bacteria; yeasts; Drosophila, *C. elegans* and other invertebrates; mammalian cells of many types; and whole mammalian organisms (mice). Two extensively characterized site-specific recombination systems are the cre recombinase and its target lox site (ataacttcgtataatgtatgctatacg aagttat) (SEQ ID NO:1), and the FLP recombinase and its target FRT site (GAAGTTCCTATTCTCTAGAAAGTATAGGAACTTC) (SEQ ID NO:5), but other systems exist as well, such as pSR1 from *Zygosaccharomyces rouxii*. Recombinase can be provided to CD-tagged cells in a number of ways. For example a gene encoding the recombinase can be delivered to the tagged cell by transfection or by infection with a recombinant virus containing the gene (e.g., pAdv/Cre, Wang et al. (1996)). Or the recombinase gene can be provided by crossing a transgenic animal carrying the CD-tagged gene to an animal that expresses recombinase; excision of the exon will then occur in those cells of the zygote in which recombinase is expressed (Lasko et al. (1992, 1996); Gu et al. (1994); Rajewsky et al. (1996)).

Generation of Frameshift Mutations Using Recombinase Target Sites in the Intronic Portions of the CD-Cassette When tandem CD-cassettes are present in a gene, and when one of the CD-cassettes contains a pair of site-specific recombinase target sites surrounding its guest exon, then when recombinase activity is expressed in a cell containing the tagged gene the result is excision of the exon surrounded by the sites. To take advantage of this fact to create frameshift mutations in the tagged gene, the two guest exons are designed to encode compensatory frameshift mutations; in particular, one guest exon contains 3N+1 nucleotides (where N is a whole number) and the other contains 3N−1 nucleotides. As a result, when both guest exons are included within the mRNA there is no frameshift of the translational reading frame downstream of the CD cassette inserts. When one of the two guest exons is removed via expression of recombinase and the excision of one of the guest exons, however, a frameshift of the reading frame downstream of the cassettes is created.

One embodiment is constructed and employed as follows. Two new CD-cassettes are created by site specific mutation of the CD-1 cassette of Jarvik et al. (1996). In one (called CD-1+) an adenosine is added between C-168 and T-169. In the other (called CD-1−)C-168 is deleted. Oligonucleotides containing lox sites are synthesized by standard methods and inserted into CD-1+ at the Cla-1 site (position 74) and at the SphI site (position 203) by standard methods. The modified CD-1+ and CD-1− are inserted in tandem into the NsiI site in intron 3 of the Chlamydomonas pf14 gene in plasmid pKE-RS3 following the procedures described in Jarvik et al. (1996). A doubly tagged plasmid with the CD-1+ cassette upstream of the CD-1− cassette at the NsiI site is identified and named pRSO3+/−.

pRSO3+/− is transformed into the cre-expressing *E. coli* strain NS3516, and plasmid is isolated from a clone of transformed cells and shown by sequencing analysis to have lost the CD-1+ cassette and to retain a single lox site. This plasmid is named pRSO3−/cre. In separate transformations, Chlamydomonas cells carrying a pf14 ochre mutation are transformed with plasmid pKE-RS3 (Jarvik et al. (1996)), plasmid pRSO3−/1 and plasmid pRSO3−/cre. Cells that contain the plasmid DNA are identified by PCR analysis. The cells containing the wild type pf14 gene (plasmid pKE-RS3) and those that contain plasmid pRSO3+/− are observed to have acquired motile flagella, indicating that the tagged RSP3 protein expressed from the pRSO3+− DNA is functional. Immunofluorescence analysis with antibody 12CA5 shows immunostaining of the flagella in the transformants, and Western blot analysis shows the presence of a protein about 4 kD larger than native RSP3 (pf14 gene product). In contrast, the transformants that contain the pRSO3−/cre plasmid are not motile and their flagella are not immunostained with antibody 12CA5, indicating that the cells do not contain functional RSP3. Western blot analysis shows that the cells contain an immunoreactive protein that is less than half the molecular weight of native RSP3. The experiment demonstrates that when a gene is CD-tagged with tandem CD-cassettes that carry compensatory frameshift mutations, the result is an addition of tandem guest peptides to the gene product without loss of native amino acids. When one of the guest exons is subsequently excised, a frameshift mutation and the consequent premature chain termination of the gene product results. The predicted amino acid sequences of the RSP3 species encoded in each construct are shown below. The amino acids introduced by nucleotides in the guest exons are underlined and the amino acids encoded out of frame in the pf14 sequence after site specific recombination are shown in italics. An asterisk indicates the position of a nonsense codon.

Native RSP3 516aa(SEQ ID NO:2)

MVQAKAQQQLYTHAAEPKAVQQRRAKYREDETTQTL
PTANIMFDRRVVRGNTYAARILPADATQTQTKGPSP
ASTKKRTTRTLPPRTPEAVDGRRHIDIQTDVYLEEL
TDTVPEADTSTQTDAFLDRPPTPLFVPQKTGTDAIT
QIENDLFDFDFEVEPILEVLVGKVLEQGLMEVLEE
EELAAMRAHQEHFEQIRNAELVATQRMEAAERRKLE
EKERRMQQERERVERERVVRQKVAASAFARGYLSGI
VNTVFDRLVSSGYIYDPVMREVETAFMPWLKEQATG
YLARGVVARRVVDKLVEDAAAALAANRSTLADKAAS
TAATVDAWAERQAKMEAELQGKELEAVRRRPTFVLR
ELKPAVASADAVEAAAAELTAQAEEAANAKWEADKA
EAAEKARAEAEAAAEEQKALLEELAATAAAEAEERG
EEPPAEPPSLPDGVEPVDVEAEVAKAVEAVPKPPVK
EVTDIDILSYMMDKGAITKDAIIQALAVHALGDKAY
TNHPAFAEAEGA*

Tandem tagged RSP3 552aa(SEQ ID NO:3)

MVQAKAQQQLYTHAAEPKAVQQRRAKYREDETTQTL
PTANIMFDRRVVRGNTYAARILPADATQTQTKGPSP
ASTKKRTTRTLPPRTPEAVDGRRHIDIQTDVYLEEL
TDTVPEADTSTQTDAFLDRPPTPLFVPQKTGTDAIT
QIENGGRARYPYDVPDYATKIIRWKSSVPLRRPRLR
HEDSGDLFDFDFEVEPILEVLVGKVLEQGLMEVLEE
EELAANRAHQEHFEQIRNAELVATQRMEAAERRKLE
EKERRMQQERERVERERVVRQKVAASAFARGYLSGI
VNTVFDRLVSSGYIYDPVMREVETAFMPWLKEQAIG
YLARGVVARRVVDKLVEDAAAALAANRSTLADKAAS
TAATVDAWAERQAKMEAELQGKELEAVRRRPTFVLR
ELKPAVASADAVEAAAAELTAQAEEAANAKWEADKA
EAAEKARAEAEAAAEEQKALLEELAATAAAEAEERG
EEPPAEPPSLPDGVEPVDVEAEVAKAVEAVPKPPVK
EVTDIDILSYMMDKGAITKDAIIQALAVHALGDKAY
TNHPAFAEAEAFGA*

Frameshift RSPB 191aa(SEQ ID NO:4)

MVQAKAQQQLYTHAAEPKAVQQRRAKYREDETTQTL
PTANIMFDRRVVRGNTYAARILPADATQTQTKGPSP
ASTKKRTTRTLPPRTPEAVDGRRHIDIQTDVYLEEL
TDTVPEADTSTQTDAFLDRPPTPLFVPQKTGTDAIT
QIENGGRARYPYDVPDYATKIQVTCLTLTSRWSPSW
RCWWARCWSRA*

Construction of GeneFinder-1, a CD-Cassette Delivery Vector with Frameshift Generation Capability for Use in Drosophila Melanogaster The new vector GeneFinder-1 is designed so that once a gene is tagged one can readily produce a frameshift mutation in it in vivo using FLP-recombinase. GeneFinder-1 carries two epitope-encoding CD-cassettes, with the 5' exon 3N−1 nucleotides in length and the 3' exon 3N+1 nucleotides. Surrounding the downstream exon are FRT sites that serve to delete the exon in vivo when the strain is crossed to one expressing FLP-recombinase (Golic and Lindquist (1989)). The result will be a frameshift mutation in the gene. The FRT sites will be situated so that the vermillion gene is deleted as well, allowing us to readily identify individuals that have deleted the DNA between the FRT sites on the basis of eye color.

Figure 11:
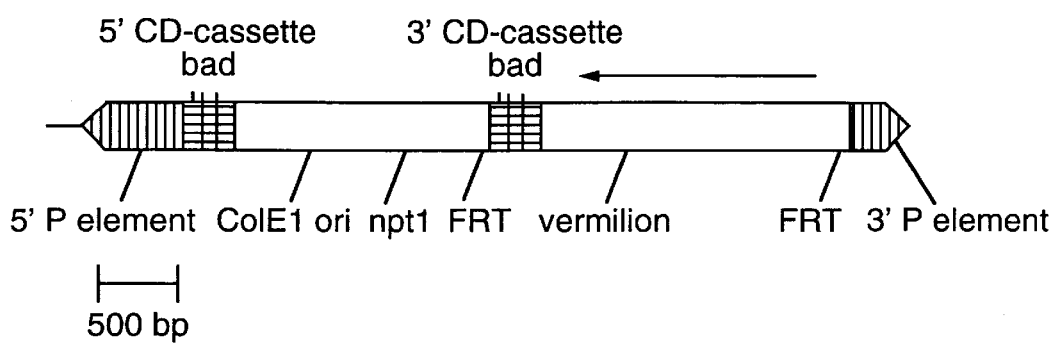
FIG. 11 is an illustration of the "GeneFinder-1" according to the present invention.

The structure of GeneFinder-1 is shown in FIG. 11.

To construct the 5' cassette, pCD-0 (described in Jarvik et al. (1996)) is opened at its SacI site near the 5' end of the guest exon and ligated to a 20-fold molar excess of the two synthetic 11-mers, 5' caattggagct 3' (SEQ ID NO: 6) and 5'ccaattgagct 3' (SEQ ID NO: 7)(which base pair to form a SacI-to-SacI linker with an internal MunI site). The ligated DNA is cut with MunI, religated, and transformed into *E. coli*. Plasmids are prepared from Ampr colonies and tested for the presence of a MunI restriction site at the former SacI site. The guest exon in the 5' CD-cassette is 65 nt (3N−1) in length. To construct the 3' cassette, pCD-1 (Jarvik et al. (1996)) is opened at the BglII site near the 3' end of its guest exon and ligated to a 20-fold molar excess of the synthetic 10-mer oligonucleotide 5' gatcccatgg 3' (which base pairs to form a BglII-to-BglII linker with an internal NcoI site). The ligated DNA is cut with NcoI, religated, and transformed into *E. coli*. Plasmids are prepared from Ampr colonies and tested for the presence of a NcoI restriction site at the former BglII site. The guest exon in the 3' CD-cassette is 64 nt (3N+1) in length.

Construction of the GeneFinder-1 element begins with plasmid pYC1.8, which contains a 1.8 kb vermillion gene surrounded by P element ends (Fridell and Searles (1991)). A 34nt FRT sequence with HindIII sticky ends, obtained by combining two 38nt oligonucleotides, is inserted in the HindIII site upstream of the vermilion insert. The 5' CD-cassette is cut with EcoRI and the fragment is inserted at the polylinker EcoRI site of the pYC1.8 derivative. Recombinant plasmids are recovered and tested to identify one with the CD-cassette oriented opposite to the direction of transcription of vermilion. This plasmid is opened with SalI and the SalI fragment of the 3' cassette inserted to produce a plasmid with tandem CD-cassettes. Prior to this step, an FRT site is inserted into the 3' cassette at the PacI site. Finally, npt1 (Kanr) ColE1-ori fragment from plasmid pUC4K is inserted into the NotI site to produce the complete GeneFinder-1 vector.

Before using GeneFinder to identify new genes, it is confirmed that it functions as expected by inserting it into Ubx and testing the construct as described in Jarvik et al. (1996). This is done by PCR amplifying the entire GeneFinder element (minus the P element ends) using primers with XbaI sites at their 5' ends, and inserting the amplicon into the XbaI site of the Ubx-containing plasmid pUMG101. The resulting plasmid contains both the white gene from pUMG101 and the vermilion gene from GeneFinder-1. It carries just one pair of P element ends—those that surround white and Ubx. The plasmid is injected along with the transposase-donating plasmid pp25.7 into two sets of Drosophila embryos: a white mutant to identify transformants on the basis of white expression, and a vermillion, rosy mutant (v36fry506) to identify transformants on the basis of vermilion expression. White+ transformant embryos are tested for expression of epitope-tagged Ubx protein after crossing to a GAL4-expressing strain (Jarvik et al. (1996)). Epitope-tagged Ubx protein is observed, indicating that GeneFinder is a functional CD-tagging vector. Observation of vermilion+ transformants is also observed, indicating that the vermilion gene is expressed from GeneFinder. Finally, v+ transformants express epitope tagged Ubx protein, indicating that expression of vermilion does not interfere with expression of the guest exons from the opposite DNA strand.

Establishment of Lines Carrying X-Linked Recessive-Lethal GeneFinder Insertions

GeneFinder-1 DNA is injected into v36fyl ry506 embryos along with the transposase-donating plasmid pp25.7. Surviving adults are crossed to v36fyl ry506 and germline transposants among the progeny are identified on the basis of dull red (v+, ry506), instead of peach (v36fry506) eye color. Twenty or more independent female transposants are crossed again to v36fyl ry506 and the progeny inspected to identify cases in which all of the red-eyed progeny are female, indicating that there is a recessive-lethal insertion of GeneFinder-1 into the X-chromosome.

Mobilization of GeneFinder-1 to New Chromosomal Locations

To mobilize GeneFinder-1, red-eyed females obtained as described above are crossed to a v36fyl strain carrying the TMS balancer which contains the P[ry+D2-3] element (Robertson et al. (1988)). Female progeny (genotype P[GF-1]v36fyl/v36fyl; P[ry+D2-3] ry2 Sb/ry506) are crossed to v36fy+ry506 males. The male progeny (which can be recognized immediately by their yellow body color due to the X-lined yl mutation in addition to the normal sexually dimorphic characters) are primarily of two types: those that have received the TMS second chromosome and have scarlet eyes due to the v36f allele on X and the ry+ gene in the D2-3 P element, and those that have received the second chromosome with the ry506 mutation and therefore have peach eyes. On occasion, however, there are also Sb+ males that express v+. These carry GF-1 transpositions to new chromosomes and the transpositions are stable because they have lost the maternal (D2-3) second chromosome.

Pilot Transposition Screens to Identify a Suitable GeneFinder Donor

Several recessive lethal transposants of GeneFinder to X are tested to find one that transposes to other chromosomes with relatively high frequency under the influence of D2-3. For each strain the first cross is performed as described above and several virgin female progeny are placed in individual bottles along with a similar number of v36fy+ry506 males. Approximately fifteen days later the progeny in each bottle are examined for yellow non-stubble males with dark red eyes. Individual lines are established from these animals by crossing to a v36f strain. To ensure that all transposition lines are independent, only one line is established from each bottle. Finally, to confirm that the lines truly carry transpositions to new chromosomes, rather than reversion of the recessive-lethal mutation, (e.g., by excisions that restore gene function), the pattern of segregation of v+ in the lines is noted. Since most of the transpositions to new chromosomes should be the autosomes, vermillion does not segregate in a sex-linked manner in most v+ derivatives of the desired line. Once a GeneFinder strain from which the vector is readily mobilized is found, it is used to isolate transposition lines in large numbers, using the screen described in the previous paragraph.

Generation of Lines Homozygous for New GeneFinder Insertions

As new transposition lines are obtained, they are crossed with v−/v (CyO;MKRS)/Xasta females, and red-eyed males and virgin females carrying the CyO and MKRS balancer chromosomes are isolated and mated inter se. Inspection of progeny from these crosses serves to assign each insertion to a particular chromosome (X,2,3 or 4) based on the pattern of segregation and reveals whether the autosomal insertions are lethal (no homozygotes) or produce a visible phenotype when homozygous. For X-linked transpositions, viable male-fertile insertions are recovered, and visible phenotypes, if they exist, are uncovered by hemizygosity in the red-eyed males. Lethal autosomal insertions are discarded. Homozygous stocks of the viable insertions are established from the homozygous progeny of the cross that will be identified because they lack the appropriate balancer homolog.

Generation of Frameshift Mutations in the Tagged Genes

Frameshift mutations are created beginning with the homozygous GeneFinder transposition lines generated as follows. First they are crossed to a strain that carries v– and ry–mutations and FLP38, a chromosome 3 MKRS balancer within which resides a P element with an ry+ marker gene and a FLP-recombinase gene under the control of the hsp70 heat shock promoter (Chou and Perrimon (1992)). Progeny carrying GeneFinder and the FLP38 chromosome are identified on the basis of their wild type eye color and the dominant markers on the balancer. These animals are subjected to a heat shock regime (Golic and Lindguist (1989)) and allowed to mate inter se. F2 progeny are screened to identify those with ry+ v– eye color; these animals have lost the 3' guest exon by recombination between their FRT sites. As a result, the CD-tagged mRNA is now frameshifted beginning immediately downstream of the 65 nt 5' guest exon; in the great majority of cases this inactivates the gene product and produces a recessive mutation. (If the frameshift mutation is a dominant lethal, of course, there is a failure to obtain ry+ v–F2 animals altogether, and if it has a dominant visible phenotype it is apparent by inspection of the mutants.) To determine the homozygous phenotype of the frameshift mutations, the ry+ v– flies are crossed inter se and their progeny inspected.

The presence of ry– v– progeny in the F3 indicates that the mutation is not homozygous lethal; in such cases adults, larvae and embryos are observed closely to see if there is a visible nonlethal phenotype. The fertility of these flies is also examined, because some mutations are male or female sterile. The absence of ry– v– progeny in the F3 indicates that the mutaton is a lethal. In these cases the pupal, larval and embryonic stages are examined closely to identify the lethal stage and to determine the way in which the defect is expressed morphologically. Furthermore, because the truncated protein resulting from the frameshift mutation retains a guest epitope, it is worthwhile to immunostain the mutant organisms, including, in the recessive lethal cases, those that are dying or destined to die. Immunostaining is particularly informative in the cases where the original CD-tagged protein showed tissue or organ specific expression. Since the truncated protein, though inactive, serves to mark the very tissues in which its function is required.

The mutant analysis has an additional formal virtue. For each gene for which FLP-recombinase creates a recessive lethal mutation, it can be concluded that the original CD-tagged gene did in fact retain activity. Thus, the mutant data will allow us to reach explicit conclusions about the frequency with which CD-tagging a gene does, or does not, destroy its function.

Removing Function-Inactivating Mutations

In the cases described up to now, the CD-tagged gene is initially tagged with a construct that does not alter the translational reading frame, and, by subsequent provision of recombinase activity, a frameshift is created. But the situation can be readily reversed, i.e., the tagging construct can create a frameshift, and subsequent provision of recombinase can remove it, leaving a functional CD-tagged gene. This is accomplished in the following manner. The CD-tagging construct has two tandem CD-cassettes, as before, but now one of the guest exons has 3N+1 or 3N–1 nucleotides and the other has 3N. Recombinase target sites are provided flanking the 3N+1 or 3N–1 exon. Thus, when both exons are present a frameshift occurs, and when recombinase activity is provided the frameshift is removed.

The specific descriptions presented above should be construed as exemplifications of certain embodiments of my invention and are not intended to limit its scope. Many other variations and applications are possible. For example, the guest exon that is excised by recombinase could encode an enzymatic activity (e.g., neomycin phosphotransferase or beta-galactosidase) or some other function (e.g., Green Fluorescent Protein or a substrate for biotin ligase activity) or it could contain translational stop codons. Accordingly, the scope of the invention should be determined not by the embodiments illustrated here but by the appended claims and their legal equivalents.

Conclusion, Ramifications and Scope of Invention

In conclusion, this invention describes a method for tagging gene, transcript and protein in a single recombinational event. This method has unique and highly useful advantages over all other methods with similar aims in the prior art.

The specific description of my invention presented above should not be construed as limiting its scope, but rather as exemplification of certain embodiments thereof. Many other variations and applications are possible. For example, peptides could be designed that have sites that lead to specific covalent modification of the tagged protein—either by a small molecule or a macromolecule. Or the peptide tag could contain a site for hydrolysis of a peptide bond by an inducible protease, thereby making it possible to assess the function of the tagged gene in vivo. Or CD-DNAs could contain cis-acting sites for the inducible activation of transcription arranged so that inhibitory anti-sense transcripts from the target gene are produced, thereby making it possible to assess the function of the tagged gene in vivo. Or the peptide-encoding sequence could contain nucleotides that are hypermutable in vivo so as to promote mutations such as frameshifts that could inactivate protein function. Or an enhancer of transcription could be included within the CD-DNA so that expression of the target gene is stimulated by the CD-DNA. Accordingly, the scope of the invention should be determined not by the embodiments illustrated here but by the appended claims and their legal equivalents.

I claim:

1. A method for tagging genes, transcripts and proteins in cells, comprising:

(1) producing a tagged gene by inserting a DNA sequence into an intron of a gene by:

(a) selecting a DNA sequence (i) having a 5' portion free of any nucleotide sequence selected from the group consisting of CAGGTAAGT, CAGGTGAGT, AAGGTAAGT, AAGGTGAGT;

(ii) a nucleotide sequence selected from the group consisting of TACTAAC, TGCTAAC, TCCTAAC, TTCTAAC, TACTGAC, TGCTGAC, TCCTGAC, TTCTGAC and TACTAAC, and any nucleotide sequence identical to a known splice branch site in a known gene, followed by;

(iii) a sequence selected from the group consisting of a sequence 14 to 34 nucleotides in length and any nucleotide sequence identical in length to a known spacer region between splice branch and acceptor sites in a known gene, followed by;

(iv) a nucleotide sequence selected from the group consisting of CAGG, TAGG and any sequence identical to a known splice acceptor site in a known gene, followed by;

(v) an open reading frame 3N-1 nucleotides in length, said open reading frame encoding a known peptide tag recognizable by a known reaction characteristic of said known peptide tag, followed by;

(vi) a nucleotide sequence selected from the group consisting of CAGGTAAGT, CAGGTGAGT, AAGGTAAGT, AAGGTGAGT and any sequence identical to a known splice donor site in a known gene; and (b) inserting said DNA sequence into said intron within said gene to create a tagged gene; and (2) incubating said tagged gene within a cell so as to maintain intact or to introduce said tagged gene within the genome of said cell.

2. The method of claim 1 wherein said DNA sequence is introduced into said intron by in vitro recombination methods.

3. The method of claim 1 wherein said DNA sequence is introduced into said intron by in vivo recombination.

4. The method of claim 1 wherein said cell is that of a microorganism.

5. The method of claim 1 wherein said cell belongs to a culture of pleuripotent stem cells derived from a multicellular organism.

6. The method of claim 1 wherein said cell belongs to a somatic cell culture derived from a multicellular organism.

7. The method of claim 1 wherein expression of said gene is promoted by introducing said DNA sequence into said cell by a method chosen from the following group: transformation, electroporation, transduction, transfection, viral infection, bulk loading and liposome fusion.

8. The method of claim 1 wherein said DNA sequence is introduced into said intron by the method of transposon insertion.

9. The method of claim 1 wherein said DNA sequence is part of a recombinant plasmid.

10. The method of claim 1 wherein said DNA sequence is part of a recombinant virus.

11. The method of claim 1 wherein said DNA sequence is part of a recombinant transposon.

12. The method of claim 1 wherein said DNA sequence becomes stably incorporated into the genome of said cell.

13. The method of claim 1 wherein said peptide tag is recognized by specific monoclonal antibodies.

14. The method of claim 1 wherein said peptide tag is recognized by specific polyclonal antibodies.

15. The method of claim 1 wherein said peptide tag is recognized by specific reagents that are not antibodies.

16. The method of claim 1 wherein said gene is contained in a living cell.

17. The method of claim 1 wherein said gene is contained in isolated genomic, viral or organelle DNA.

18. The method according to claim 1 wherein said open reading frame encodes a polypeptide sequence chosen from the group consisting of neomycin phosphotransferase, beta-galactosidase, green fluorescent protein and a substrate for biotin ligase.

19. A method for tagging genes, transcripts and proteins in cells, comprising:

(1) producing a tagged gene by inserting a DNA sequence into an intron of a gene by:

(a) selecting a first DNA sequence (i) having a 5' portion free of any nucleotide sequence selected from the group consisting of CAGGTAAGT, CAGGTGAGT, AAGGTAAGT, AAGGTGAGT;

(ii) a nucleotide sequence selected from the group consisting of TACTAAC, TGCTAAC, TCCTAAC, TTCTAAC, TACTGAC, TGCTGAC, TCCTGAC, TTCTGAC and TACTAAC, and any nucleotide sequence identical to a known splice branch site in a known gene, followed by;

(iii) a sequence selected from the group consisting of a sequence 14 to 34 nucleotides in length and any nucleotide sequence identical in length to a known spacer region between splice branch and acceptor sites in a known gene, followed by;

(iv) a nucleotide sequence selected from the group consisting of CAGG, TAGG and any sequence identical to a known splice acceptor site in a known gene, followed by;

(v) an open reading frame 3N nucleotides in length, said open reading frame encoding a known peptide tag recognizable by a known reaction characteristic of said known peptide tag, followed by;

(vi) a nucleotide sequence selected from the group consisting of CAGGTAAGT, CAGGTGAGT, AAGGTAAGT, AAGGTGAGT and any sequence identical to a known splice donor site in a known gene;
(b) selecting a second DNA sequence
(i) having a 5' portion free of any nucleotide sequence selected from the group consisting of CAGGTAAGT, CAGGTGAGT, AAGGTAAGT, AAGGTGAGT;
(ii) a nucleotide sequence selected from the group consisting of TACTAAC, TGCTAAC, TCCTAAC, TTCTAAC, TACTGAC, TGCTGAC, TCCTGAC, TTCTGAC and TACTAAC, and any nucleotide sequence identical to a known splice branch site in a known gene, followed by;
(iii) a sequence selected from the group consisting of a sequence 14 to 34 nucleotides in length and any nucleotide sequence identical in length to a known spacer region between splice branch and acceptor sites in a known gene, followed by;
(iv) a nucleotide sequence selected from the group consisting of CAGG, TAGG and any sequence identical to a known splice acceptor site in a known gene, followed by;
(v) an open reading frame 3N+1 nucleotides in length, said open reading frame encoding a known peptide tag recognizable by a known reaction characteristic of said known peptide tag, followed by;
(vi) a nucleotide sequence selected from the group consisting of CAGGTAAGT, CAGGTGAGT, AAGGTAAGT, AAGGTGAGT and any sequence identical to a known splice donor site in a known gene; and
(c) inserting said first and second DNA sequences in tandem into said intron within said gene to create a tagged gene; and
(2) incubating said tagged gene within a cell so as to maintain intact or to introduce said tagged gene within the genome of said cell.

20. The method of claim 19 wherein said DNA sequence is introduced into said intron by in vitro recombination methods.

21. The method of claim 19 wherein said DNA sequence is introduced into said intron by in vivo recombination.

22. The method of claim 19 wherein said cell is that of a microorganism.

23. The method of claim 19 wherein said cell belongs to a culture of pleuripotent stem cells derived from a multicellular organism.

24. The method of claim 19 wherein said cell belongs to a somatic cell culture derived from a multicellular organism.

25. The method of claim 19 wherein expression of said gene is promoted by introducing said DNA sequence into said cell by a method chosen from the following group: transformation, electroporation, transduction, transfection, viral infection, bulk loading and liposome fusion.

26. The method of claim 19 wherein said DNA sequence is introduced into said intron by the method of transposon insertion.

27. The method of claim 19 wherein said DNA sequence is part of a recombinant plasmid.

28. The method of claim 19 wherein said DNA sequence is part of a recombinant virus.

29. The method of claim 19 wherein said DNA sequence is part of a recombinant transposon.

30. The method of claim 19 wherein said DNA sequence becomes stably incorporated into the genome of said cell.

31. The method of claim 19 wherein said peptide tag is recognized by specific monoclonal antibodies.

32. The method of claim 19 wherein said peptide tag is recognized by specific polyclonal antibodies.

33. The method of claim 19 wherein said peptide tag is recognized by specific reagents that are not antibodies.

34. The method of claim 19 wherein said gene is contained in a living cell.

35. The method of claim 19 wherein said gene is contained in isolated genomic, viral or organelle DNA.

36. The method according to claim 19 wherein said first sequence is 5' to said second sequence.

37. The method according to claim 19 wherein said first sequence is 3' to said second sequence.

38. The method according to claim 19 wherein said first or second sequence is flanked by nucleotide sequences known to be recombinogenic.

39. The method according to claim 38 wherein the recombinogenic sequences are lox sites.

40. The method according to claim 38 wherein the recombinogenic sequences are FRT sites.

41. A method for creating a frameshift mutation in a gene in a cell by tagging said gene by the method of claim 38 followed by the activation of the recombinogenic sequences so as to delete said sequence flanked by the recombinogenic sequences.

42. The method according to claim 41 wherein the activation of the recombinogenic sequences is catalyzed by cre recombinase.

43. The method according to claim 41 wherein the activation of said recombinogenic sequences is catalyzed by FLP recombinase.

44. The method according to claim 19 wherein one or both of said open reading frames encode a polypeptide sequence chosen from the group consisting of neomycin phosphotransferase, beta-galactosidase, green fluorescent protein and a substrate for biotin ligase.

45. A method for tagging genes, transcripts and proteins in cells, comprising:
(1) producing a tagged gene by inserting a DNA sequence into an intron of a gene by:
(a) selecting a first DNA sequence
(i) having a 5' portion free of any nucleotide sequence selected from the group consisting of CAGGTAAGT, CAGGTGAGT, AAGGTAAGT, AAGGTGAGT;
(ii) a nucleotide sequence selected from the group consisting of TACTAAC, TGCTAAC, TCCTAAC, TTCTAAC, TACTGAC, TGCTGAC, TCCTGAC, TTCTGAC and TACTAAC, and any nucleotide sequence identical to a known splice branch site in a known gene, followed by;
(iii) a sequence selected from the group consisting of a sequence 14 to 34 nucleotides in length and any nucleotide sequence identical in length to a known spacer region between splice branch and acceptor sites in a known gene, followed by;
(iv) a nucleotide sequence selected from the group consisting of CAGG, TAGG and any sequence identical to a known splice acceptor site in a known gene, followed by;
(v) an open reading frame 3N−1 nucleotides in length, said open reading frame encoding a known peptide tag recognizable by a known reaction characteristic of said known peptide tag, followed by;

(vi) a nucleotide sequence selected from the group consisting of CAGGTAAGT, CAGGTGAGT, AAGGTAAGT, AAGGTGAGT and any sequence identical to a known splice donor site in a known gene;
(b) selecting a second DNA sequence
(i) having a 5' portion free of any nucleotide sequence selected from the group consisting of CAGGTAAGT, CAGGTGAGT, AAGGTAAGT, AAGGTGAGT;
(ii) a nucleotide sequence selected from the group consisting of TACTAAC, TGCTAAC, TCCTAAC, TTCTAAC, TACTGAC, TGCTGAC, TCCTGAC, TTCTGAC and TACTAAC, and any nucleotide sequence identical to a known splice branch site in a known gene, followed by;
(iii) a sequence selected from the group consisting of a sequence 14 to 34 nucleotides in length and any nucleotide sequence identical in length to a known spacer region between splice branch and acceptor sites in a known gene, followed by;
(iv) a nucleotide sequence selected from the group consisting of CAGG, TAGG and any sequence identical to a known splice acceptor site in a known gene, followed by;
(v) an open reading frame 3N or 3N+1 nucleotides in length, said open reading frame encoding a known peptide tag recognizable by a known reaction characteristic of said known peptide tag, followed by;
(vi) a nucleotide sequence selected from the group consisting of CAGGTAAGT, CAGGTGAGT, AAGGTAAGT, AAGGTGAGT and any sequence identical to a known splice donor site in a known gene; and
(c) inserting said first and second DNA sequences in tandem into said intron within said gene to create a tagged gene; and
(2) incubating said tagged gene within a cell so as to maintain intact or to introduce said tagged gene within the genome of said cell.

46. The method of claim 45 wherein said DNA sequence is introduced into said intron by in vitro recombination methods.

47. The method of claim 45 wherein said DNA sequence is introduced into said intron by in vivo recombination.

48. The method of claim 45 wherein said cell is that of a microorganism.

49. The method of claim 45 wherein said cell belongs to a culture of pleuripotent stem cells derived from a multicellular organism.

50. The method of claim 45 wherein said cell belongs to a somatic cell culture derived from a multicellular organism.

51. The method of claim 45 wherein expression of said gene is promoted by introducing said DNA sequence into said cell by a method chosen from the following group: transformation, electroporation, transduction, transfection, viral infection, bulk loading and liposome fusion.

52. The method of claim 45 wherein said DNA sequence is introduced into said intron by the method of transposon insertion.

53. The method of claim 45 wherein said DNA sequence is part of a recombinant plasmid.

54. The method of claim 45 wherein said DNA sequence is part of a recombinant virus.

55. The method of claim 45 wherein said DNA sequence is part of a recombinant transposon.

56. The method of claim 45 wherein said DNA sequence becomes stably incorporated into the genome of said cell.

57. The method of claim 45 wherein said peptide tag is recognized by specific monoclonal antibodies.

58. The method of claim 45 wherein said peptide tag is recognized by specific polyclonal antibodies.

59. The method of claim 45 wherein said peptide tag is recognized by specific reagents that are not antibodies.

60. The method of claim 45 wherein said gene is contained in a living cell.

61. The method of claim 45 wherein said gene is contained in isolated genomic, viral or organelle DNA.

62. The method according to claim 45 wherein said first sequence is 5' to said second sequence.

63. The method according to claim 45 wherein said first sequence is 3' to said second sequence.

64. The method according to claim 45 wherein said first or second sequence is flanked by nucleotide sequences known to be recombinogenic.

65. The method according to claim 64 wherein the recombinogenic sequences are lox sites.

66. The method according to claim 64 wherein the recombinogenic sequences are FRT sites.

67. A method for creating a frameshift mutation in a gene in a cell by tagging said gene by the method of claim 64 followed by the activation of the recombinogenic sequences so as to delete said sequence flanked by the recombinogenic sequences.

68. The method according to claim 64 wherein the activation of the recombinogenic sequences is catalyzed by cre recombinase.

69. The method according to claim 64 wherein the activation of the recombinogenic sequences is catalyzed by FLP recombinase.

70. The method according to claim 45 wherein one or both of said open reading frames encode a polypeptide sequence chosen from the group consisting of neomycin phosphotransferase, beta-galactosidase, green fluorescent protein and a substrate for biotin ligase.

71. A method for tagging genes, transcripts and proteins in cells, comprising:
(1) producing a tagged gene by inserting a DNA sequence into an intron of a gene by:
(a) selecting a first DNA sequence
(i) having a 5' portion free of any nucleotide sequence selected from the group consisting of CAGGTAAGT, CAGGTGAGT, AAGGTAAGT, AAGGTGAGT;
(ii) a nucleotide sequence selected from the group consisting of TACTAAC, TGCTAAC, TCCTAAC, TTCTAAC, TACTGAC, TGCTGAC, TCCTGAC, TTCTGAC and TACTAAC, and any nucleotide sequence identical to a known splice branch site in a known gene, followed by;
(iii) a sequence selected from the group consisting of a sequence 14 to 34 nucleotides in length and any nucleotide sequence identical in length to a known spacer region between splice branch and acceptor sites in a known gene, followed by;
(iv) a nucleotide sequence selected from the group consisting of CAGG, TAGG and any sequence identical to a known splice acceptor site in a known gene, followed by;
(v) an open reading frame 3N−1 nucleotides in length, said open reading frame encoding a known peptide tag recognizable by a known reaction characteristic of said known peptide tag, followed by;

(vi) a nucleotide sequence selected from the group consisting of CAGGTAAGT, CAGGTGAGT, AAGGTAAGT, AAGGTGAGT and any sequence identical to a known splice donor site in a known gene;
(b) selecting a second DNA sequence
(i) having a 5' portion free of any nucleotide sequence selected from the group consisting of CAGGTAAGT, CAGGTGAGT, AAGGTAAGT, AAGGTGAGT;
(ii) a nucleotide sequence selected from the group consisting of TACTAAC, TGCTAAC, TCCTAAC, TTCTAAC, TACTGAC, TGCTGAC, TCCTGAC, TTCTGAC and TACTAAC, and any nucleotide sequence identical to a known splice branch site in a known gene, followed by;
(iii) a sequence selected from the group consisting of a sequence 14 to 34 nucleotides in length and any nucleotide sequence identical in length to a known spacer region between splice branch and acceptor sites in a known gene, followed by;
(iv) a nucleotide sequence selected from the group consisting of CAGG, TAGG and any sequence identical to a known splice acceptor site in a known gene, followed by;
(v) a sequence of nucleotides containing one or more stop codons in one or more reading frames;
(vi) a nucleotide sequence selected from the group consisting of CAGGTAAGT, CAGGTGAGT, AAGGTAAGT, AAGGTGAGT and any sequence identical to a known splice donor site in a known gene; and
(c) inserting said first and second DNA sequences in tandem into said intron within said gene to create a tagged gene; and
(2) incubating said tagged gene within a cell so as to maintain intact or to introduce said tagged gene within the genome of said cell.

72. The method of claim 71 wherein said DNA sequence is introduced into said intron by in vitro recombination methods.

73. The method of claim 71 wherein said DNA sequence is introduced into said intron by in vivo recombination.

74. The method of claim 71 wherein said cell is that of a microorganism.

75. The method of claim 71 wherein said cell belongs to a culture of pleuripotent stem cells derived from a multicellular organism.

76. The method of claim 71 wherein said cell belongs to a somatic cell culture derived from a multicellular organism.

77. The method of claim 71 wherein expression of said gene is promoted by introducing said DNA sequence into said cell by a method chosen from the following group: transformation, electroporation, transfection, bulk loading and liposome fusion.

78. The method of claim 71 wherein said DNA sequence is introduced into said intron by the method of transposon insertion.

79. The method of claim 71 wherein said DNA sequence is part of a recombinant plasmid.

80. The method of claim 71 wherein said DNA sequence is part of a recombinant virus.

81. The method of claim 71 wherein said DNA sequence is part of a recombinant transposon.

82. The method of claim 71 wherein said DNA sequence becomes stably incorporated into the genome of said cell.

83. The method of claim 71 wherein said peptide tag is recognized by specific monoclonal antibodies.

84. The method of claim 71 wherein said peptide tag is recognized by specific polyclonal antibodies.

85. The method of claim 71 wherein said peptide tag is recognized by specific reagents that are not antibodies.

86. The method of claim 71 wherein said gene is contained in a living cell.

87. The method of claim 71 wherein said gene is contained in isolated genomic, viral or organelle DNA.

88. The method according to claim 71 wherein said first sequence is 5' to said second sequence.

89. The method according to claim 71 wherein said first sequence is 3' to said second sequence.

90. The method according to claim 71 wherein said first or second sequence is flanked by nucleotide sequences known to be recombinogenic.

91. The method according to claim 90 wherein the recombinogenic sequences are lox sites.

92. The method according to claim 90 wherein the recombinogenic sequences are FRT sites.

93. A method for eliminating a nonsense mutation in a gene by tagging said gene by the method of claim 90 followed by the activation of the recombinogenic sequences so as to delete said sequence flanked by the recombinogenic sequences.

94. The method according to claim 93 wherein the activation of the recombinogenic sequences is catalyzed by cre recombinase.

95. The method according to claim 93 wherein the activation of the recombinogenic sequences is catalyzed by FLP recombinase.

96. The method according to claim 71 wherein said open reading frame or said sequence of nucleotides containing one or more stop codons encode a polypeptide sequence chosen from the group consisting of neomycin phosphotransferase, beta-galactosidase, green fluorescent protein and a substrate for biotin ligase.

97. A eukaryotic cell containing at least one gene tagged in accordance with the method of claim 1.

98. A eukaryotic cell containing at least one gene tagged in accordance with the method of claim 19.

99. A eukaryotic cell containing at least one gene tagged in accordance with the method of claim 45.

100. A eukaryotic cell containing at least one gene tagged in accordance with the method of claim 71.

* * * * *

UNITED STATES PATENT AND TRADEMARK OFFICE
CERTIFICATE OF CORRECTION

PATENT NO. : 6,096,717
DATED : August 1, 2000
INVENTOR(S) : JONATHAN W. JARVIK

It is certified that error appears in the above-identified patent and that said Letters Patent is hereby corrected as shown below:

Title Page [54] after "GENES" insert --,--.

Title Page [76] Inventor: "Pittsburg" should read --Pittsburgh--.

Column 1 Line 1 after "GENES" insert --,--.

Column 6 Line 36 "molecules; and" should read --molecules;--.

Column 6 Line 38 "intron." should read --intron;--.

Column 6 Line 40 "intron." should read --intron; and--.

Column 8 Line 64 "Peotides" should read --Peptides--.

Column 12 Line 30 last two letters "TG" should read --IG--.

Column 12 Line 51 last four characters "FGA*" should read --EGA*--.

Column 12 Line 53 "RSPB" should read --RSP3--.

Claim 43 Column 28 Line 31 "said" should read --the--.

Claim 68 Column 30 Line 27 "64" should read --67--.

Claim 69 Column 30 Line 30 "64" should read --67--.

Signed and Sealed this

Twenty-fourth Day of April, 2001

Attest:

NICHOLAS P. GODICI

*Attesting Officer*    *Acting Director of the United States Patent and Trademark Office*

SEQUENCE LISTING

<160> NUMBER OF SEQ ID NOS: 7

<210> SEQ ID NO 1
<211> LENGTH: 27
<212> TYPE: DNA
<213> ORGANISM: P1 phage
<220> FEATURE:
<221> NAME/KEY: misc_recomb
<222> LOCATION: (1)...(27)
<223> OTHER INFORMATION: lox target of cre recombinase

<400> SEQUENCE: 1
ataacttcgt ataatgtatg ctatacg     27

<210> SEQ ID NO 2
<211> LENGTH: 516
<212> TYPE: PRT
<213> ORGANISM: Chlamydomonas

<400> SEQUENCE: 2

Met Val Gln Ala Lys Ala Gln Gln Gln Leu Tyr Thr His Ala Ala Glu
 1               5                  10                  15

Pro Lys Ala Val Gln Gln Arg Arg Ala Lys Tyr Arg Glu Asp Glu Thr
                20                  25                  30

Thr Gln Thr Leu Pro Thr Ala Asn Ile Met Phe Asp Arg Arg Val Val
            35                  40                  45

Arg Gly Asn Thr Tyr Ala Ala Arg Ile Leu Pro Ala Asp Ala Thr Gln
        50                  55                  60

Thr Gln Thr Lys Gly Pro Ser Pro Ala Ser Thr Lys Lys Arg Thr Thr
65                  70                  75                  80

Arg Thr Leu Pro Pro Arg Thr Pro Glu Ala Val Asp Gly Arg His
                85                  90                  95

Ile Asp Ile Gln Thr Asp Val Tyr Leu Glu Glu Leu Thr Asp Thr Val
                100                 105                 110

Pro Glu Ala Asp Thr Ser Thr Gln Thr Asp Ala Phe Leu Asp Arg Pro
            115                 120                 125

Pro Thr Pro Leu Phe Val Pro Gln Lys Thr Gly Thr Asp Ala Ile Thr
        130                 135                 140

Gln Ile Glu Asn Gly Asp Leu Phe Asp Phe Asp Phe Glu Val Glu Pro
145                 150                 155                 160

Ile Leu Glu Val Leu Val Gly Lys Val Leu Glu Gln Gly Leu Met Glu
                165                 170                 175

Val Leu Glu Glu Glu Leu Ala Ala Met Arg Ala His Gln Glu His
            180                 185                 190

Phe Glu Gln Ile Arg Asn Ala Glu Leu Val Ala Thr Gln Arg Met Glu
        195                 200                 205

Ala Ala Glu Arg Arg Lys Leu Glu Lys Glu Arg Arg Met Gln Gln
    210                 215                 220

Glu Arg Glu Arg Val Glu Arg Glu Arg Val Val Arg Gln Lys Val Ala
225                 230                 235                 240

Ala Ser Ala Phe Ala Arg Gly Tyr Leu Ser Gly Ile Val Asn Thr Val
                245                 250                 255

Phe Asp Arg Leu Val Ser Ser Gly Tyr Ile Tyr Asp Pro Val Met Arg
            260                 265                 270

Glu Val Glu Thr Ala Phe Met Pro Trp Leu Lys Glu Gln Ala Ile Gly
        275                 280                 285

-continued

```
Tyr Leu Ala Arg Gly Val Val Ala Arg Val Asp Lys Leu Val
    290                 295                 300

Glu Asp Ala Ala Ala Leu Ala Asn Arg Ser Thr Leu Ala Asp
305                 310                 315                 320

Lys Ala Ala Ser Thr Ala Ala Thr Val Asp Ala Trp Ala Glu Arg Gln
                325                 330                 335

Ala Lys Met Glu Ala Glu Leu Gln Gly Lys Glu Leu Glu Ala Val Arg
            340                 345                 350

Arg Arg Pro Thr Phe Val Leu Arg Glu Leu Lys Pro Ala Val Ala Ser
            355                 360                 365

Ala Asp Ala Val Glu Ala Ala Ala Glu Leu Thr Ala Gln Ala Glu
    370                 375                 380

Glu Ala Ala Asn Ala Lys Trp Glu Ala Asp Lys Ala Glu Ala Ala Glu
385                 390                 395                 400

Lys Ala Arg Ala Glu Ala Glu Ala Ala Glu Glu Gln Lys Ala Leu
            405                 410                 415

Leu Glu Glu Leu Ala Ala Thr Ala Ala Ala Glu Ala Glu Arg Gly
            420                 425                 430

Glu Glu Pro Pro Ala Glu Pro Pro Ser Leu Pro Asp Gly Val Glu Pro
            435                 440                 445

Val Asp Val Glu Ala Glu Val Ala Lys Ala Val Glu Ala Val Pro Lys
    450                 455                 460

Pro Pro Val Lys Glu Val Thr Asp Ile Asp Ile Leu Ser Tyr Met Met
465                 470                 475                 480

Asp Lys Gly Ala Ile Thr Lys Asp Ala Ile Ile Gln Ala Leu Ala Val
            485                 490                 495

His Ala Leu Gly Asp Lys Ala Tyr Thr Asn His Pro Ala Phe Ala Glu
            500                 505                 510

Ala Glu Gly Ala
            515

<210> SEQ ID NO 3
<211> LENGTH: 552
<212> TYPE: PRT
<213> ORGANISM: Chlamydomonas

<400> SEQUENCE: 3

Met Val Gln Ala Lys Ala Gln Gln Leu Tyr Thr His Ala Ala Glu
1               5                   10                  15

Pro Lys Ala Val Gln Gln Arg Ala Lys Tyr Arg Glu Asp Glu Thr
            20                  25                  30

Thr Gln Thr Leu Pro Thr Ala Asn Ile Met Phe Asp Arg Val Val
        35                  40                  45

Arg Gly Asn Thr Tyr Ala Ala Arg Ile Leu Pro Ala Asp Ala Thr Gln
 50                 55                  60

Thr Gln Thr Lys Gly Pro Ser Pro Ala Ser Lys Lys Arg Thr Thr
65                  70                  75                  80

Arg Thr Leu Pro Pro Arg Thr Pro Glu Ala Val Asp Gly Arg His
            85                  90                  95

Ile Asp Ile Gln Thr Asp Val Tyr Leu Glu Glu Leu Thr Asp Thr Val
            100                 105                 110

Pro Glu Ala Asp Thr Ser Thr Gln Thr Asp Ala Phe Leu Asp Arg Pro
        115                 120                 125

Pro Thr Pro Leu Phe Val Pro Gln Lys Thr Gly Thr Asp Ala Ile Thr
```

```
                130                 135                 140
Gln Ile Glu Asn Gly Gly Arg Ala Arg Tyr Pro Tyr Asp Val Pro Asp
145                 150                 155                 160
Tyr Ala Thr Lys Ile Ile Arg Trp Lys Ser Ser Val Pro Leu Arg Arg
                165                 170                 175
Pro Arg Leu Arg His Glu Asp Ser Gly Asp Leu Phe Asp Phe Asp Phe
            180                 185                 190
Glu Val Glu Pro Ile Leu Glu Val Leu Val Gly Lys Val Leu Glu Gln
            195                 200                 205
Gly Leu Met Glu Val Leu Glu Glu Glu Leu Ala Ala Met Arg Ala
210                 215                 220
His Gln Glu His Phe Glu Gln Ile Arg Asn Ala Glu Leu Val Ala Thr
225                 230                 235                 240
Gln Arg Met Glu Ala Ala Glu Arg Arg Lys Leu Glu Glu Lys Glu Arg
                245                 250                 255
Arg Met Gln Gln Glu Arg Glu Arg Val Glu Arg Glu Arg Val Val Arg
            260                 265                 270
Gln Lys Val Ala Ala Ser Ala Phe Ala Arg Gly Tyr Leu Ser Gly Ile
            275                 280                 285
Val Asn Thr Val Phe Asp Arg Leu Val Ser Ser Gly Tyr Ile Tyr Asp
290                 295                 300
Pro Val Met Arg Glu Val Glu Thr Ala Phe Met Pro Trp Leu Lys Glu
305                 310                 315                 320
Gln Ala Ile Gly Tyr Leu Ala Arg Gly Val Ala Arg Arg Val Val
                325                 330                 335
Asp Lys Leu Val Glu Asp Ala Ala Ala Leu Ala Ala Asn Arg Ser
            340                 345                 350
Thr Leu Ala Asp Lys Ala Ala Ser Thr Ala Thr Val Asp Ala Trp
            355                 360                 365
Ala Glu Arg Gln Ala Lys Met Glu Ala Glu Leu Gln Gly Lys Glu Leu
            370                 375                 380
Glu Ala Val Arg Arg Arg Pro Thr Phe Val Leu Arg Glu Leu Lys Pro
385                 390                 395                 400
Ala Val Ala Ser Ala Asp Ala Val Glu Ala Ala Ala Glu Leu Thr
                405                 410                 415
Ala Gln Ala Glu Glu Ala Ala Asn Ala Lys Trp Glu Ala Asp Lys Ala
            420                 425                 430
Glu Ala Ala Glu Lys Ala Arg Ala Glu Ala Ala Ala Glu Glu
            435                 440                 445
Gln Lys Ala Leu Leu Glu Glu Leu Ala Ala Thr Ala Ala Glu Ala
            450                 455                 460
Glu Glu Arg Gly Glu Glu Pro Pro Ala Glu Pro Pro Ser Leu Pro Asp
465                 470                 475                 480
Gly Val Glu Pro Val Asp Val Glu Ala Glu Val Ala Lys Ala Val Glu
            485                 490                 495
Ala Val Pro Lys Pro Pro Val Lys Glu Val Thr Asp Ile Asp Ile Leu
            500                 505                 510
Ser Tyr Met Met Asp Lys Gly Ala Ile Thr Lys Asp Ala Ile Ile Gln
            515                 520                 525
Ala Leu Ala Val His Ala Leu Gly Asp Lys Ala Tyr Thr Asn His Pro
            530                 535                 540
Ala Phe Ala Glu Ala Glu Gly Ala
545                 550
```

<210> SEQ ID NO 4
<211> LENGTH: 191
<212> TYPE: PRT
<213> ORGANISM: Chlamydomonas

<400> SEQUENCE: 4

Met Val Gln Ala Lys Ala Gln Gln Gln Leu Tyr Thr His Ala Ala Glu
 1               5                  10                  15

Pro Lys Ala Val Gln Gln Arg Arg Ala Lys Tyr Arg Glu Asp Glu Thr
            20                  25                  30

Thr Gln Thr Leu Pro Thr Ala Asn Ile Met Phe Asp Arg Arg Val Val
        35                  40                  45

Arg Gly Asn Thr Tyr Ala Ala Arg Ile Leu Pro Ala Asp Ala Thr Gln
 50                  55                  60

Thr Gln Thr Lys Gly Pro Ser Pro Ala Ser Thr Lys Lys Arg Thr Thr
 65                  70                  75                  80

Arg Thr Leu Pro Pro Arg Thr Pro Glu Ala Val Asp Gly Arg Arg His
                85                  90                  95

Ile Asp Ile Gln Thr Asp Val Tyr Leu Glu Glu Leu Thr Asp Thr Val
            100                 105                 110

Pro Glu Ala Asp Thr Ser Thr Gln Thr Asp Ala Phe Leu Asp Arg Pro
        115                 120                 125

Pro Thr Pro Leu Phe Val Pro Gln Lys Thr Gly Thr Asp Ala Ile Thr
130                 135                 140

Gln Ile Glu Asn Gly Gly Arg Ala Arg Tyr Pro Tyr Asp Val Pro Asp
145                 150                 155                 160

Tyr Ala Thr Lys Ile Gln Val Thr Cys Leu Thr Leu Thr Ser Arg Trp
                165                 170                 175

Ser Pro Ser Trp Arg Cys Trp Ala Arg Cys Trp Ser Arg Ala
            180                 185                 190

<210> SEQ ID NO 5
<211> LENGTH: 34
<212> TYPE: DNA
<213> ORGANISM: 2mu phage
<220> FEATURE:
<221> NAME/KEY: misc_recomb
<222> LOCATION: (1)...(34)
<223> OTHER INFORMATION: FRT target site of FLP recombinase

<400> SEQUENCE: 5
gaagttccta ttctctagaa agtataggaa cttc                              34

<210> SEQ ID NO 6
<211> LENGTH: 11
<212> TYPE: DNA
<213> ORGANISM: Artificial Sequence
<220> FEATURE:
<223> OTHER INFORMATION: First strand of SacI-MunI-SacI linker

<400> SEQUENCE: 6
caattggagc t                                                   11

<210> SEQ ID NO 7
<211> LENGTH: 11
<212> TYPE: DNA

-continued

```
<213> ORGANISM: Artificial Sequence
<220> FEATURE:
<223> OTHER INFORMATION: Second strand of SacI-MunI-SacI linker

<400> SEQUENCE: 7
ccaattgagc t                                                              11
```